United States Patent
Swift

(10) Patent No.: US 6,617,104 B2
(45) Date of Patent: *Sep. 9, 2003

(54) PREDISPOSITION TO BREAST CANCER BY MUTATIONS AT THE ATAXIA-TELANGIECTASIA GENETIC LOCUS

(76) Inventor: Michael R. Swift, 227 Underhill Rd., Scarsdale, NY (US) 10583

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/984,090

(22) Filed: Dec. 3, 1997

(65) Prior Publication Data

US 2001/0021502 A1 Sep. 13, 2001

Related U.S. Application Data

(60) Provisional application No. 60/032,435, filed on Dec. 3, 1996.

(51) Int. Cl.[7] .............. C12Q 1/68; C12P 19/34; C07H 21/04; C07H 21/02
(52) U.S. Cl. .......... 435/6; 435/91.1; 435/91.2; 536/23.1; 536/23.5; 536/24.31; 536/24.33
(58) Field of Search ............. 435/6, 91.2, 7.1, 435/91.1, 91.3; 536/23.5, 24.31, 24.33, 23.1

(56) References Cited

FOREIGN PATENT DOCUMENTS

| WO | 9605308 | 2/1996 |
| WO | 9722689 | 6/1997 |

OTHER PUBLICATIONS

Platzer et al., Genome Research, vol. 7, pp 592–607, 1997.*
Swift, et al. (1991) N. Engl. J. Med. 325: 1831–1836.*
Vorechovsky et al. Cancer Res (Jun. 1996) 56: 2726–2732.*
Vorechovsky et al. Can. Res (Sep. 1996) 56:4130–4133.*
Fitzgerald et al. Nature Genet. 15: 307–310 (1997).*
Chen et al. Can. Res. (Apr. 1998) 58: 1376–1379.*
Telatar et al. Am. J. Hum. Genet. 62: 86–97 (1998).*
Telatar et al. Mol. Genet. Metab. 64: 36–43 (1998).*
Stankovic et al. Am. V. Hum. Genet. 62: 334–345 (1998).*
Chen, J. *Cancer Research* vol. 60 pp. 5037–5039 (Sep. 2000).
Gatei, M., et al. *Cancer Research* vol. 60 pp. 3299–3304 (Jun. 2000).
Shangary, S., et al. *J. of Biological Chemistry* 275:39 pp. 30163–30168 (Sep. 2000).
Ahn, J., et al., *Cancer Research* vol. 60 pp. 5934–5936 (Nov. 2000).
Kim, S., et al., *J. of Biological Chemistry* 274:53 pp. 37538–37543 (Dec. 1999).
Savitsky, K., et al., *Science* vol. 268 pp. 1749–1753 (Jun. 1995).
Cortez, D., et al. *Science* vol. 286 pp. 1162–1166 (Nov. 1999).
Vorechovsky et al., "The *ATM* Gene and Susceptibility to Breast Cancer: Analysis of 38 Breast Tumors Reveals No Evidence for Mutation", *Cancer Res.*, 56:2726–2732 (Jun. 15, 1996).

* cited by examiner

*Primary Examiner*—Jehanne Souaya
(74) *Attorney, Agent, or Firm*—McKenna Long & Aldridge LLP

(57) ABSTRACT

The present invention relates generally to the field of human genetics. Specifically, the present invention relates to the discovery that some alleles of the A-T gene cause susceptibility to cancer, in particular breast cancer. More specifically, the present invention relates to germline mutations in the A-T gene and their use in the diagnosis of predisposition to breast cancer. The invention further relates to somatic mutations in the A-T gene in human breast cancer and their use in the diagnosis and prognosis of human breast cancer.

12 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 9196 base pairs
      (B) TYPE: nucleic acid
      (C) STRANDEDNESS: single
      (D) TOPOLOGY: linear (ii) MOLECULE TYPE: cDNA -continued (ix) FEATURE:
(A) NAME/KEY: CDS
(B) LOCATION: 1..9168

(xi) SEQUENCE DESCRIPTION: SEQ ID NO:1:

```
ATG AGT CTA GTA CTT AAT GAT CTG CTT ATC TGC TGC CGT CAA CTA GAA      48
Met Ser Leu Val Leu Asn Asp Leu Leu Ile Cys Cys Arg Gln Leu Glu
 1               5                  10                  15

CAT GAT AGA GCT ACA GAA CGA AAG AAA GAA GTT GAG AAA TTT AAG CGC      96
His Asp Arg Ala Thr Glu Arg Lys Lys Glu Val Glu Lys Phe Lys Arg
            20                  25                  30

CTG ATT CGA GAT CCT GAA ACA ATT AAA CAT CTA GAT CGG CAT TCA GAT     144
Leu Ile Arg Asp Pro Glu Thr Ile Lys His Leu Asp Arg His Ser Asp
        35                  40                  45

TCC AAA CAA GGA AAA TAT TTG AAT TGG GAT GCT GTT TTT AGA TTT TTA     192
Ser Lys Gln Gly Lys Tyr Leu Asn Trp Asp Ala Val Phe Arg Phe Leu
 50                  55                  60

CAG AAA TAT ATT CAG AAA GAA ACA GAA TGT CTG AGA ATA GCA AAA CCA     240
Gln Lys Tyr Ile Gln Lys Glu Thr Glu Cys Leu Arg Ile Ala Lys Pro
 65                  70                  75                  80

AAT GTA TCA GCC TCA ACA CAA GCC TCC AGG CAG AAA AAG ATG CAG GAA     288
Asn Val Ser Ala Ser Thr Gln Ala Ser Arg Gln Lys Lys Met Gln Glu
             85                  90                  95

ATC AGT AGT TTG GTC AAA TAC TTC ATC AAA TGT GCA AAC AGA AGA GCA     336
Ile Ser Ser Leu Val Lys Tyr Phe Ile Lys Cys Ala Asn Arg Arg Ala
            100                 105                 110

CCT AGG CTA AAA TGT CAA GAA CTC TTA AAT TAT ATC ATG GAT ACA GTG     384
Pro Arg Leu Lys Cys Gln Glu Leu Leu Asn Tyr Ile Met Asp Thr Val
        115                 120                 125

AAA GAT TCA TCT AAT GGT GCT ATT TAC GGA GCT GAT TGT AGC AAC ATA     432
Lys Asp Ser Ser Asn Gly Ala Ile Tyr Gly Ala Asp Cys Ser Asn Ile
130                 135                 140

CTA CTC AAA GAC ATT CTT TCT GTG AGA AAA TAC TGG TGT GAA ATA TCT     480
Leu Leu Lys Asp Ile Leu Ser Val Arg Lys Tyr Trp Cys Glu Ile Ser
145                 150                 155                 160

CAG CAA CAG TGG TTA GAA TTG TTC TCT GTG TAC TTC AGG CTC TAT CTG     528
Gln Gln Gln Trp Leu Glu Leu Phe Ser Val Tyr Phe Arg Leu Tyr Leu
                165                 170                 175

AAA CCT TCA CAA GAT GTT CAT AGA GTT TTA GTG GCT AGA ATA ATT CAT     576
Lys Pro Ser Gln Asp Val His Arg Val Leu Val Ala Arg Ile Ile His
            180                 185                 190

GCT GTT ACC AAA GGA TGC TGT TCT CAG ACT GAC GGA TTA AAT TCC AAA     624
Ala Val Thr Lys Gly Cys Cys Ser Gln Thr Asp Gly Leu Asn Ser Lys
        195                 200                 205

TTT TTG GAC TTT TTT TCC AAG GCT ATT CAG TGT GCG AGA CAA GAA AAG     672
Phe Leu Asp Phe Phe Ser Lys Ala Ile Gln Cys Ala Arg Gln Glu Lys
210                 215                 220

AGC TCT TCA GGT CTA AAT CAT ATC TTA GCA GCT CTT ACT ATC TTC CTC     720
Ser Ser Ser Gly Leu Asn His Ile Leu Ala Ala Leu Thr Ile Phe Leu
225                 230                 235                 240

AAG ACT TTG GCT GTC AAC TTT CGA ATT CGA GTG TGT GAA TTA GGA GAT     768
Lys Thr Leu Ala Val Asn Phe Arg Ile Arg Val Cys Glu Leu Gly Asp
                245                 250                 255

GAA ATT CTT CCC ACT TTG CTT TAT ATT TGG ACT CAA CAT AGG CTT AAT     816
Glu Ile Leu Pro Thr Leu Leu Tyr Ile Trp Thr Gln His Arg Leu Asn
            260                 265                 270

GAT TCT TTA AAA GAA GTC ATT ATT GAA TTA TTT CAA CTG CAA ATT TAT     864
Asp Ser Leu Lys Glu Val Ile Ile Glu Leu Phe Gln Leu Gln Ile Tyr
        275                 280                 285

ATC CAT CAT CCG AAA GGA GCC AAA ACC CAA GAA AAA GGT GCT TAT GAA     912
```

```
                    Ile His His Pro Lys Gly Ala Lys Thr Gln Glu Lys Gly Ala Tyr Glu
                        290                 295                 300

TCA ACA AAA TGG AGA AGT ATT TTA TAC AAC TTA TAT GAT CTG CTA GTG            960
Ser Thr Lys Trp Arg Ser Ile Leu Tyr Asn Leu Tyr Asp Leu Leu Val
305                 310                 315                 320

AAT GAG ATA AGT CAT ATA GGA AGT AGA GGA AAG TAT TCT TCA GGA TTT           1008
Asn Glu Ile Ser His Ile Gly Ser Arg Gly Lys Tyr Ser Ser Gly Phe
                325                 330                 335

CGT AAT ATT GCC GTC AAA GAA AAT TTG ATT GAA TTG ATG GCA GAT ATC           1056
Arg Asn Ile Ala Val Lys Glu Asn Leu Ile Glu Leu Met Ala Asp Ile
                340                 345                 350

TGT CAC CAG GTT TTT AAT GAA GAT ACC AGA TCC TTG GAG ATT TCT CAA           1104
Cys His Gln Val Phe Asn Glu Asp Thr Arg Ser Leu Glu Ile Ser Gln
                355                 360                 365

TCT TAC ACT ACT ACA CAA AGA GAA TCT AGT GAT TAC AGT GTC CCT TGC           1152
Ser Tyr Thr Thr Thr Gln Arg Glu Ser Ser Asp Tyr Ser Val Pro Cys
370                 375                 380

AAA AGG AAG AAA ATA GAA CTA GGC TGG GAA GTA ATA AAA GAT CAC CTT           1200
Lys Arg Lys Lys Ile Glu Leu Gly Trp Glu Val Ile Lys Asp His Leu
385                 390                 395                 400

CAG AAG TCA CAG AAT GAT TTT GAT CTT GTG CCT TGG CTA CAG ATT GCA           1248
Gln Lys Ser Gln Asn Asp Phe Asp Leu Val Pro Trp Leu Gln Ile Ala
                405                 410                 415

ACC CAA TTA ATA TCA AAG TAT CCT GCA AGT TTA CCT AAC TGT GAG CTG           1296
Thr Gln Leu Ile Ser Lys Tyr Pro Ala Ser Leu Pro Asn Cys Glu Leu
                420                 425                 430

TCT CCA TTA CTG ATG ATA CTA TCT CAG CTT CTA CCC CAA CAG CGA CAT           1344
Ser Pro Leu Leu Met Ile Leu Ser Gln Leu Leu Pro Gln Gln Arg His
                435                 440                 445

GGG GAA CGT ACA CCA TAT GTG TTA CGA TGC CTT ACG GAA GTT GCA TTG           1392
Gly Glu Arg Thr Pro Tyr Val Leu Arg Cys Leu Thr Glu Val Ala Leu
450                 455                 460

TGT CAA GAC AAG AGG TCA AAC CTA GAA AGC TCA CAA AAG TCA GAT TTA           1440
Cys Gln Asp Lys Arg Ser Asn Leu Glu Ser Ser Gln Lys Ser Asp Leu
465                 470                 475                 480

TTA AAA CTC TGG AAT AAA ATT TGG TGT ATT ACC TTT CGT GGT ATA AGT           1488
Leu Lys Leu Trp Asn Lys Ile Trp Cys Ile Thr Phe Arg Gly Ile Ser
                485                 490                 495

TCT GAG CAA ATA CAA GCT GAA AAC TTT GGC TTA CTT GGA GCC ATA ATT           1536
Ser Glu Gln Ile Gln Ala Glu Asn Phe Gly Leu Leu Gly Ala Ile Ile
                500                 505                 510

CAG GGT AGT TTA GTT GAG GTT GAC AGA GAA TTC TGG AAG TTA TTT ACT           1584
Gln Gly Ser Leu Val Glu Val Asp Arg Glu Phe Trp Lys Leu Phe Thr
                515                 520                 525

GGG TCA GCC TGC AGA CCT TCA TGT CCT GCA GTA TGC TGT TTG ACT TTG           1632
Gly Ser Ala Cys Arg Pro Ser Cys Pro Ala Val Cys Cys Leu Thr Leu
530                 535                 540

GCA CTG ACC ACC AGT ATA GTT CCA GGA GCG GTA AAA ATG GGA ATA GAG           1680
Ala Leu Thr Thr Ser Ile Val Pro Gly Ala Val Lys Met Gly Ile Glu
545                 550                 555                 560

CAA AAT ATG TGT GAA GTA AAT AGA AGC TTT TCT TTA AAG GAA TCA ATA           1728
Gln Asn Met Cys Glu Val Asn Arg Ser Phe Ser Leu Lys Glu Ser Ile
                565                 570                 575

ATG AAA TGG CTC TTA TTC TAT CAG TTA GAG GGT GAC TTA GAA AAT AGC           1776
Met Lys Trp Leu Leu Phe Tyr Gln Leu Glu Gly Asp Leu Glu Asn Ser
                580                 585                 590

ACA GAA GTG CCT CCA ATT CTT CAC AGT AAT TTT CCT CAT CTT GTA CTG           1824
Thr Glu Val Pro Pro Ile Leu His Ser Asn Phe Pro His Leu Val Leu
                595                 600                 605
```

```
GAG AAA ATT CTT GTG AGT CTC ACT ATG AAA AAC TGT AAA GCT GCA ATG          1872
Glu Lys Ile Leu Val Ser Leu Thr Met Lys Asn Cys Lys Ala Ala Met
    610                 615                 620

AAT TTT TTC CAA AGC GTG CCA GAA TGT GAA CAC CAC CAA AAA GAT AAA          1920
Asn Phe Phe Gln Ser Val Pro Glu Cys Glu His His Gln Lys Asp Lys
625                 630                 635                 640

GAA GAA CTT TCA TTC TCA GAA GTA GAA GAA CTA TTT CTT CAG ACA ACT          1968
Glu Glu Leu Ser Phe Ser Glu Val Glu Glu Leu Phe Leu Gln Thr Thr
                645                 650                 655

TTT GAC AAG ATG GAC TTT TTA ACC ATT GTG AGA GAA TGT GGT ATA GAA          2016
Phe Asp Lys Met Asp Phe Leu Thr Ile Val Arg Glu Cys Gly Ile Glu
            660                 665                 670

AAG CAC CAG TCC AGT ATT GGC TTC TCT GTC CAC CAG AAT CTC AAG GAA          2064
Lys His Gln Ser Ser Ile Gly Phe Ser Val His Gln Asn Leu Lys Glu
        675                 680                 685

TCA CTG GAT CGC TGT CTT CTG GGA TTA TCA GAA CAG CTT CTG AAT AAT          2112
Ser Leu Asp Arg Cys Leu Leu Gly Leu Ser Glu Gln Leu Leu Asn Asn
    690                 695                 700

TAC TCA TCT GAG ATT ACA AAT TCA GAA ACT CTT GTC CGG TGT TCA CGT          2160
Tyr Ser Ser Glu Ile Thr Asn Ser Glu Thr Leu Val Arg Cys Ser Arg
705                 710                 715                 720

CTT TTG GTG GGT GTC CTT GGC TGC TAC TGT TAC ATG GGT GTA ATA GCT          2208
Leu Leu Val Gly Val Leu Gly Cys Tyr Cys Tyr Met Gly Val Ile Ala
                725                 730                 735

GAA GAG GAA GCA TAT AAG TCA GAA TTA TTC CAG AAA GCC AAC TCT CTA          2256
Glu Glu Glu Ala Tyr Lys Ser Glu Leu Phe Gln Lys Ala Asn Ser Leu
            740                 745                 750

ATG CAA TGT GCA GGA GAA AGT ATC ACT CTG TTT AAA AAT AAG ACA AAT          2304
Met Gln Cys Ala Gly Glu Ser Ile Thr Leu Phe Lys Asn Lys Thr Asn
        755                 760                 765

GAG GAA TTC AGA ATT GGT TCC TTG AGA AAT ATG ATG CAG CTA TGT ACA          2352
Glu Glu Phe Arg Ile Gly Ser Leu Arg Asn Met Met Gln Leu Cys Thr
    770                 775                 780

CGT TGC TTG AGC AAC TGT ACC AAG AAG AGT CCA AAT AAG ATT GCA TCT          2400
Arg Cys Leu Ser Asn Cys Thr Lys Lys Ser Pro Asn Lys Ile Ala Ser
785                 790                 795                 800

GGC TTT TTC CTG CGA TTG TTA ACA TCA AAG CTA ATG AAT GAC ATT GCA          2448
Gly Phe Phe Leu Arg Leu Leu Thr Ser Lys Leu Met Asn Asp Ile Ala
                805                 810                 815

GAT ATT TGT AAA AGT TTA GCA TCC TTC ATC AAA AAG CCA TTT GAC CGT          2496
Asp Ile Cys Lys Ser Leu Ala Ser Phe Ile Lys Lys Pro Phe Asp Arg
            820                 825                 830

GGA GAA GTA GAA TCA ATG GAA GAT GAT ACT AAT GGA AAT CTA ATG GAG          2544
Gly Glu Val Glu Ser Met Glu Asp Asp Thr Asn Gly Asn Leu Met Glu
        835                 840                 845

GTG GAG GAT CAG TCA TCC ATG AAT CTA TTT AAC GAT TAC CCT GAT AGT          2592
Val Glu Asp Gln Ser Ser Met Asn Leu Phe Asn Asp Tyr Pro Asp Ser
    850                 855                 860

AGT GTT AGT GAT GCA AAC GAA CCT GGA GAG AGC CAA AGT ACC ATA GGT          2640
Ser Val Ser Asp Ala Asn Glu Pro Gly Glu Ser Gln Ser Thr Ile Gly
865                 870                 875                 880

GCC ATT AAT CCT TTA GCT GAA GAA TAT CTG TCA AAG CAA GAT CTA CTT          2688
Ala Ile Asn Pro Leu Ala Glu Glu Tyr Leu Ser Lys Gln Asp Leu Leu
                885                 890                 895

TTC TTA GAC ATG CTC AAG TTC TTG TGT TTG TGT GTA ACT ACT GCT CAG          2736
Phe Leu Asp Met Leu Lys Phe Leu Cys Leu Cys Val Thr Thr Ala Gln
            900                 905                 910

ACC AAT ACT GTG TCC TTT AGG GCA GCT GAT ATT CGG AGG AAA TTG TTA          2784
Thr Asn Thr Val Ser Phe Arg Ala Ala Asp Ile Arg Arg Lys Leu Leu
        915                 920                 925
```

```
ATG TTA ATT GAT TCT AGC ACG CTA GAA CCT ACC AAA TCC CTC CAC CTG         2832
Met Leu Ile Asp Ser Ser Thr Leu Glu Pro Thr Lys Ser Leu His Leu
        930                 935                 940

CAT ATG TAT CTA ATG CTT TTA AAG GAG CTT CCT GGA GAA GAG TAC CCC         2880
His Met Tyr Leu Met Leu Leu Lys Glu Leu Pro Gly Glu Glu Tyr Pro
945                 950                 955                 960

TTG CCA ATG GAA GAT GTT CTT GAA CTT CTG AAA CCA CTA TCC AAT GTG         2928
Leu Pro Met Glu Asp Val Leu Glu Leu Leu Lys Pro Leu Ser Asn Val
                965                 970                 975

TGT TCT TTG TAT CGT CGT GAC CAA GAT GTT TGT AAA ACT ATT TTA AAC         2976
Cys Ser Leu Tyr Arg Arg Asp Gln Asp Val Cys Lys Thr Ile Leu Asn
        980                 985                 990

CAT GTC CTT CAT GTA GTG AAA AAC CTA GGT CAA AGC AAT ATG GAC TCT         3024
His Val Leu His Val Val Lys Asn Leu Gly Gln Ser Asn Met Asp Ser
        995                 1000                1005

GAG AAC ACA AGG GAT GCT CAA GGA CAG TTT CTT ACA GTA ATT GGA GCA         3072
Glu Asn Thr Arg Asp Ala Gln Gly Gln Phe Leu Thr Val Ile Gly Ala
        1010                1015                1020

TTT TGG CAT CTA ACA AAG GAG AGG AAA TAT ATA TTC TCT GTA AGA ATG         3120
Phe Trp His Leu Thr Lys Glu Arg Lys Tyr Ile Phe Ser Val Arg Met
1025                1030                1035                1040

GCC CTA GTA AAT TGC CTT AAA ACT TTG CTT GAG GCT GAT CCT TAT TCA         3168
Ala Leu Val Asn Cys Leu Lys Thr Leu Leu Glu Ala Asp Pro Tyr Ser
                1045                1050                1055

AAA TGG GCC ATT CTT AAT GTA ATG GGA AAA GAC TTT CCT GTA AAT GAA         3216
Lys Trp Ala Ile Leu Asn Val Met Gly Lys Asp Phe Pro Val Asn Glu
        1060                1065                1070

GTA TTT ACA CAA TTT CTT GCT GAC AAT CAT CAC CAA GTT CGC ATG TTG         3264
Val Phe Thr Gln Phe Leu Ala Asp Asn His His Gln Val Arg Met Leu
        1075                1080                1085

GCT GCA GAG TCA ATC AAT AGA TTG TTC CAG GAC ACG AAG GGA GAT TCT         3312
Ala Ala Glu Ser Ile Asn Arg Leu Phe Gln Asp Thr Lys Gly Asp Ser
        1090                1095                1100

TCC AGG TTA CTG AAA GCA CTT CCT TTG AAG CTT CAG CAA ACA GCT TTT         3360
Ser Arg Leu Leu Lys Ala Leu Pro Leu Lys Leu Gln Gln Thr Ala Phe
1105                1110                1115                1120

GAA AAT GCA TAC TTG AAA GCT CAG GAA GGA ATG AGA GAA ATG TCC CAT         3408
Glu Asn Ala Tyr Leu Lys Ala Gln Glu Gly Met Arg Glu Met Ser His
                1125                1130                1135

AGT GCT GAG AAC CCT GAA ACT TTG GAT GAA ATT TAT AAT AGA AAA TCT         3456
Ser Ala Glu Asn Pro Glu Thr Leu Asp Glu Ile Tyr Asn Arg Lys Ser
        1140                1145                1150

GTT TTA CTG ACG TTG ATA GCT GTG GTT TTA TCC TGT AGC CCT ATC TGC         3504
Val Leu Leu Thr Leu Ile Ala Val Val Leu Ser Cys Ser Pro Ile Cys
        1155                1160                1165

GAA AAA CAG GCT TTG TTT GCC CTG TGT AAA TCT GTG AAA GAG AAT GGA         3552
Glu Lys Gln Ala Leu Phe Ala Leu Cys Lys Ser Val Lys Glu Asn Gly
        1170                1175                1180

TTA GAA CCT CAC CTT GTG AAA AAG GTT TTA GAG AAA GTT TCT GAA ACT         3600
Leu Glu Pro His Leu Val Lys Lys Val Leu Glu Lys Val Ser Glu Thr
1185                1190                1195                1200

TTT GGA TAT AGA CGT TTA GAA GAC TTT ATG GCA TCT CAT TTA GAT TAT         3648
Phe Gly Tyr Arg Arg Leu Glu Asp Phe Met Ala Ser His Leu Asp Tyr
                1205                1210                1215

CTG GTT TTG GAA TGG CTA AAT CTT CAA GAT ACT GAA TAC AAC TTA TCT         3696
Leu Val Leu Glu Trp Leu Asn Leu Gln Asp Thr Glu Tyr Asn Leu Ser
        1220                1225                1230

TCT TTT CCT TTT ATT TTA TTA AAC TAC ACA AAT ATT GAG GAT TTC TAT         3744
Ser Phe Pro Phe Ile Leu Leu Asn Tyr Thr Asn Ile Glu Asp Phe Tyr
```

-continued

| | | |
|---|---|---|
| AGA TCT TGT TAT AAG GTT TTG ATT CCA CAT CTG GTG ATT AGA AGT CAT<br>Arg Ser Cys Tyr Lys Val Leu Ile Pro His Leu Val Ile Arg Ser His<br>1250                                  1255                                1260 | 3792 |
| TTT GAT GAG GTG AAG TCC ATT GCT AAT CAG ATT CAA GAG GAC TGG AAA<br>Phe Asp Glu Val Lys Ser Ile Ala Asn Gln Ile Gln Glu Asp Trp Lys<br>1265                                1270                            1275                   1280 | 3840 |
| AGT CTT CTA ACA GAC TGC TTT CCA AAG ATT CTT GTA AAT ATT CTT CCT<br>Ser Leu Leu Thr Asp Cys Phe Pro Lys Ile Leu Val Asn Ile Leu Pro<br>                      1285                            1290                           1295 | 3888 |
| TAT TTT GCC TAT GAG GGT ACC AGA GAC AGT GGG ATG GCA CAG CAA AGA<br>Tyr Phe Ala Tyr Glu Gly Thr Arg Asp Ser Gly Met Ala Gln Gln Arg<br>                   1300                            1305                        1310 | 3936 |
| GAG ACT GCT ACC AAG GTC TAT GAT ATG CTT AAA AGT GAA AAC TTA TTG<br>Glu Thr Ala Thr Lys Val Tyr Asp Met Leu Lys Ser Glu Asn Leu Leu<br>                      1315                            1320                        1325 | 3984 |
| GGA AAA CAG ATT GAT CAC TTA TTC ATT AGT AAT TTA CCA GAG ATT GTG<br>Gly Lys Gln Ile Asp His Leu Phe Ile Ser Asn Leu Pro Glu Ile Val<br>         1330                           1335                        1340 | 4032 |
| GTG GAG TTA TTG ATG ACG TTA CAT GAG CCA GCA AAT TCT AGT GCC AGT<br>Val Glu Leu Leu Met Thr Leu His Glu Pro Ala Asn Ser Ser Ala Ser<br>1345                                1350                           1355                       1360 | 4080 |
| CAG AGC ACT GAC CTC TGT GAC TTT TCA GGG GAT TTG GAT CCT GCT CCT<br>Gln Ser Thr Asp Leu Cys Asp Phe Ser Gly Asp Leu Asp Pro Ala Pro<br>                      1365                            1370                        1375 | 4128 |
| AAT CCA CCT CAT TTT CCA TCG CAT GTG ATT AAA GCA ACA TTT GCC TAT<br>Asn Pro Pro His Phe Pro Ser His Val Ile Lys Ala Thr Phe Ala Tyr<br>                   1380                            1385                        1390 | 4176 |
| ATC AGC AAT TGT CAT AAA ACC AAG TTA AAA AGC ATT TTA GAA ATT CTT<br>Ile Ser Asn Cys His Lys Thr Lys Leu Lys Ser Ile Leu Glu Ile Leu<br>         1395                           1400                        1405 | 4224 |
| TCC AAA AGC CCT GAT TCC TAT CAG AAA ATT CTT CTT GCC ATA TGT GAG<br>Ser Lys Ser Pro Asp Ser Tyr Gln Lys Ile Leu Leu Ala Ile Cys Glu<br>                   1410                            1415                        1420 | 4272 |
| CAA GCA GCT GAA ACA AAT AAT GTT TAT AAG AAG CAC AGA ATT CTT AAA<br>Gln Ala Ala Glu Thr Asn Asn Val Tyr Lys Lys His Arg Ile Leu Lys<br>1425                                1430                           1435                       1440 | 4320 |
| ATA TAT CAC CTG TTT GTT AGT TTA TTA CTG AAA GAT ATA AAA AGT GGC<br>Ile Tyr His Leu Phe Val Ser Leu Leu Leu Lys Asp Ile Lys Ser Gly<br>                   1445                            1450                        1455 | 4368 |
| TTA GGA GGA GCT TGG GCC TTT GTT CTT CGA GAC GTT ATT TAT ACT TTG<br>Leu Gly Gly Ala Trp Ala Phe Val Leu Arg Asp Val Ile Tyr Thr Leu<br>         1460                           1465                        1470 | 4416 |
| ATT CAC TAT ATC AAC CAA AGG CCT TCT TGT ATC ATG GAT GTG TCA TTA<br>Ile His Tyr Ile Asn Gln Arg Pro Ser Cys Ile Met Asp Val Ser Leu<br>                   1475                            1480                        1485 | 4464 |
| CGT AGC TTC TCC CTT TGT TGT GAC TTA TTA AGT CAG GTT TGC AGA ACA<br>Arg Ser Phe Ser Leu Cys Cys Asp Leu Leu Ser Gln Val Cys Gln Thr<br>1490                                1495                           1500 | 4512 |
| GCC GTG ACT TAC TGT AAG GAT GCT CTA GAA AAC CAT CTT CAT GTT ATT<br>Ala Val Thr Tyr Cys Lys Asp Ala Leu Glu Asn His Leu His Val Ile<br>1505                                1510                           1515                       1520 | 4560 |
| GTT GGT ACA CTT ATA CCC CTT GTG TAT GAG CAG GTG GAG GTT CAG AAA<br>Val Gly Thr Leu Ile Pro Leu Val Tyr Glu Gln Val Glu Val Gln Lys<br>                      1525                            1530                        1535 | 4608 |
| CAG GTA TTG GAC TTG TTG AAA TAC TTA GTG ATA GAT AAC AAG GAT AAT<br>Gln Val Leu Asp Leu Leu Lys Tyr Leu Val Ile Asp Asn Lys Asp Asn<br>                   1540                            1545                        1550 | 4656 |
| GAA AAC CTC TAT ATC ACG ATT AAG CTT TTA GAT CCT TTT CCT GAC CAT | 4704 |

-continued

```
Glu Asn Leu Tyr Ile Thr Ile Lys Leu Leu Asp Pro Phe Pro Asp His
        1555                1560                1565

GTT GTT TTT AAG GAT TTG CGT ATT ACT CAG CAA AAA ATC AAA TAC AGT        4752
Val Val Phe Lys Asp Leu Arg Ile Thr Gln Gln Lys Ile Lys Tyr Ser
    1570                1575                1580

AGA GGA CCC TTT TCA CTC TTG GAG GAA ATT AAC CAT TTT CTC TCA GTA        4800
Arg Gly Pro Phe Ser Leu Leu Glu Glu Ile Asn His Phe Leu Ser Val
1585                1590                1595                1600

AGT GTT TAT GAT GCA CTT CCA TTG ACA AGA CTT GAA GGA CTA AAG GAT        4848
Ser Val Tyr Asp Ala Leu Pro Leu Thr Arg Leu Glu Gly Leu Lys Asp
                1605                1610                1615

CTT CGA AGA CAA CTG GAA CTA CAT AAA GAT CAG ATG GTG GAC ATT ATG        4896
Leu Arg Arg Gln Leu Glu Leu His Lys Asp Gln Met Val Asp Ile Met
            1620                1625                1630

AGA GCT TCT CAG GAT AAT CCG CAA GAT GGG ATT ATG GTG AAA CTA GTT        4944
Arg Ala Ser Gln Asp Asn Pro Gln Asp Gly Ile Met Val Lys Leu Val
        1635                1640                1645

GTC AAT TTG TTG CAG TTA TCC AAG ATG GCA ATA AAC CAC ACT GGT GAA        4992
Val Asn Leu Leu Gln Leu Ser Lys Met Ala Ile Asn His Thr Gly Glu
    1650                1655                1660

AAA GAA GTT CTA GAG GCT GTT GGA AGC TGC TTG GGA GAA GTG GGT CCT        5040
Lys Glu Val Leu Glu Ala Val Gly Ser Cys Leu Gly Glu Val Gly Pro
1665                1670                1675                1680

ATA GAT TTC TCT ACC ATA GCT ATA CAA CAT AGT AAA GAT GCA TCT TAT        5088
Ile Asp Phe Ser Thr Ile Ala Ile Gln His Ser Lys Asp Ala Ser Tyr
                1685                1690                1695

ACC AAG GCC CTT AAG TTA TTT GAA GAT AAA GAA CTT CAG TGG ACC TTC        5136
Thr Lys Ala Leu Lys Leu Phe Glu Asp Lys Glu Leu Gln Trp Thr Phe
            1700                1705                1710

ATA ATG CTG ACC TAC CTG AAT AAC ACA CTG GTA GAA GAT TGT GTC AAA        5184
Ile Met Leu Thr Tyr Leu Asn Asn Thr Leu Val Glu Asp Cys Val Lys
        1715                1720                1725

GTT CGA TCA GCA GCT GTT ACC TGT TTG AAA AAC ATT TTA GCC ACA AAG        5232
Val Arg Ser Ala Ala Val Thr Cys Leu Lys Asn Ile Leu Ala Thr Lys
    1730                1735                1740

ACT GGA CAT AGT TTC TGG GAG ATT TAT AAG ATG ACA ACA GAT CCA ATG        5280
Thr Gly His Ser Phe Trp Glu Ile Tyr Lys Met Thr Thr Asp Pro Met
1745                1750                1755                1760

CTG GCC TAT CTA CAG CCT TTT AGA ACA TCA AGA AAA AAG TTT TTA GAA        5328
Leu Ala Tyr Leu Gln Pro Phe Arg Thr Ser Arg Lys Lys Phe Leu Glu
                1765                1770                1775

GTA CCC AGA TTT GAC AAA GAA AAC CCT TTT GAA GGC CTG GAT GAT ATA        5376
Val Pro Arg Phe Asp Lys Glu Asn Pro Phe Glu Gly Leu Asp Asp Ile
            1780                1785                1790

AAT CTG TGG ATT CCT CTA AGT GAA AAT CAT GAC ATT TGG ATA AAG ACA        5424
Asn Leu Trp Ile Pro Leu Ser Glu Asn His Asp Ile Trp Ile Lys Thr
        1795                1800                1805

CTG ACT TGT GCT TTT TTG GAC AGT GGA GGC ACA AAA TGT GAA ATT CTT        5472
Leu Thr Cys Ala Phe Leu Asp Ser Gly Gly Thr Lys Cys Glu Ile Leu
    1810                1815                1820

CAA TTA TTA AAG CCA ATG TGT GAA GTG AAA ACT GAC TTT TGT CAG ACT        5520
Gln Leu Leu Lys Pro Met Cys Glu Val Lys Thr Asp Phe Cys Gln Thr
1825                1830                1835                1840

GTA CTT CCA TAC TTG ATT CAT GAT ATT TTA CTC CAA GAT ACA AAT GAA        5568
Val Leu Pro Tyr Leu Ile His Asp Ile Leu Leu Gln Asp Thr Asn Glu
                1845                1850                1855

TCA TGG AGA AAT CTG CTT TCT ACA CAT GTT CAG GGA TTT TTC ACC AGC        5616
Ser Trp Arg Asn Leu Leu Ser Thr His Val Gln Gly Phe Phe Thr Ser
            1860                1865                1870
```

-continued

```
TGT CTT CGA CAC TTC TCG CAA ACG AGC CGA TCC ACA ACC CCT GCA AAC    5664
Cys Leu Arg His Phe Ser Gln Thr Ser Arg Ser Thr Thr Pro Ala Asn
        1875                1880                1885

TTG GAT TCA GAG TCA GAG CAC TTT TTC CGA TGC TGT TTG GAT AAA AAA    5712
Leu Asp Ser Glu Ser Glu His Phe Phe Arg Cys Cys Leu Asp Lys Lys
        1890                1895                1900

TCA CAA AGA ACA ATG CTT GCT GTT GTG GAC TAC ATG AGA AGA CAA AAG    5760
Ser Gln Arg Thr Met Leu Ala Val Val Asp Tyr Met Arg Arg Gln Lys
1905                1910                1915                1920

AGA CCT TCT TCA GGA ACA ATT TTT AAT GAT GCT TTC TGG CTG GAT TTA    5808
Arg Pro Ser Ser Gly Thr Ile Phe Asn Asp Ala Phe Trp Leu Asp Leu
        1925                1930                1935

AAT TAT CTA GAA GTT GCC AAG GTA GCT CAG TCT TGT GCT GCT CAC TTT    5856
Asn Tyr Leu Glu Val Ala Lys Val Ala Gln Ser Cys Ala Ala His Phe
        1940                1945                1950

ACA GCT TTA CTC TAT GCA GAA ATC TAT GCA GAT AAG AAA AGT ATG GAT    5904
Thr Ala Leu Leu Tyr Ala Glu Ile Tyr Ala Asp Lys Lys Ser Met Asp
        1955                1960                1965

GAT CAA GAG AAA AGA AGT CTT GCA TTT GAA GAA GGA AGC CAG AGT ACA    5952
Asp Gln Glu Lys Arg Ser Leu Ala Phe Glu Glu Gly Ser Gln Ser Thr
        1970                1975                1980

ACT ATT TCT AGC TTG AGT GAA AAA AGT AAA GAA GAA ACT GGA ATA AGT    6000
Thr Ile Ser Ser Leu Ser Glu Lys Ser Lys Glu Glu Thr Gly Ile Ser
1985                1990                1995                2000

TTA CAG GAT CTT CTC TTA GAA ATC TAC AGA AGT ATA GGG GAG CCA GAT    6048
Leu Gln Asp Leu Leu Leu Glu Ile Tyr Arg Ser Ile Gly Glu Pro Asp
        2005                2010                2015

AGT TTG TAT GGC TGT GGT GGA GGG AAG ATG TTA CAA CCC ATT ACT AGA    6096
Ser Leu Tyr Gly Cys Gly Gly Gly Lys Met Leu Gln Pro Ile Thr Arg
        2020                2025                2030

CTA CGA ACA TAT GAA CAC GAA GCA ATG TGG GGC AAA GCC CTA GTA ACA    6144
Leu Arg Thr Tyr Glu His Glu Ala Met Trp Gly Lys Ala Leu Val Thr
        2035                2040                2045

TAT GAC CTC GAA ACA GCA ATC CCC TCA TCA ACA CGC CAG GCA GGA ATC    6192
Tyr Asp Leu Glu Thr Ala Ile Pro Ser Ser Thr Arg Gln Ala Gly Ile
        2050                2055                2060

ATT CAG GCC TTG CAG AAT TTG GGA CTC TGC CAT ATT CTT TCC GTC TAT    6240
Ile Gln Ala Leu Gln Asn Leu Gly Leu Cys His Ile Leu Ser Val Tyr
2065                2070                2075                2080

TTA AAA GGA TTG GAT TAT GAA AAT AAA GAC TGG TGT CCT GAA CTA GAA    6288
Leu Lys Gly Leu Asp Tyr Glu Asn Lys Asp Trp Cys Pro Glu Leu Glu
        2085                2090                2095

GAA CTT CAT TAC CAA GCA GCA TGG AGG AAT ATG CAG TGG GAC CAT TGC    6336
Glu Leu His Tyr Gln Ala Ala Trp Arg Asn Met Gln Trp Asp His Cys
        2100                2105                2110

ACT TCC GTC AGC AAA GAA GTA GAA GGA ACC AGT TAC CAT GAA TCA TTG    6384
Thr Ser Val Ser Lys Glu Val Glu Gly Thr Ser Tyr His Glu Ser Leu
        2115                2120                2125

TAC AAT GCT CTA CAA TCT CTA AGA GAC AGA GAA TTC TCT ACA TTT TAT    6432
Tyr Asn Ala Leu Gln Ser Leu Arg Asp Arg Glu Phe Ser Thr Phe Tyr
        2130                2135                2140

GAA AGT CTC AAA TAT GCC AGA GTA AAA GAA GTG GAA GAG ATG TGT AAG    6480
Glu Ser Leu Lys Tyr Ala Arg Val Lys Glu Val Glu Glu Met Cys Lys
2145                2150                2155                2160

CGC AGC CTT GAG TCT GTG TAT TCG CTC TAT CCC ACA CTT AGC AGG TTG    6528
Arg Ser Leu Glu Ser Val Tyr Ser Leu Tyr Pro Thr Leu Ser Arg Leu
        2165                2170                2175

CAG GCC ATT GGA GAG CTG GAA AGC ATT GGG GAG CTT TTC TCA AGA TCA    6576
Gln Ala Ile Gly Glu Leu Glu Ser Ile Gly Glu Leu Phe Ser Arg Ser
        2180                2185                2190
```

-continued

```
GTC ACA CAT AGA CAA CTC TCT GAA GTA TAT ATT AAG TGG CAG AAA CAC      6624
Val Thr His Arg Gln Leu Ser Glu Val Tyr Ile Lys Trp Gln Lys His
        2195                2200                2205

TCC CAG CTT CTC AAG GAC AGT GAT TTT AGT TTT CAG GAG CCT ATC ATG      6672
Ser Gln Leu Leu Lys Asp Ser Asp Phe Ser Phe Gln Glu Pro Ile Met
2210                2215                2220

GCT CTA CGC ACA GTC ATT TTG GAG ATC CTG ATG GAA AAG GAA ATG GAC      6720
Ala Leu Arg Thr Val Ile Leu Glu Ile Leu Met Glu Lys Glu Met Asp
2225                2230                2235                2240

AAC TCA CAA AGA GAA TGT ATT AAG GAC ATT CTC ACC AAA CAC CTT GTA      6768
Asn Ser Gln Arg Glu Cys Ile Lys Asp Ile Leu Thr Lys His Leu Val
            2245                2250                2255

GAA CTC TCT ATA CTG GCC AGA ACT TTC AAG AAC ACT CAG CTC CCT GAA      6816
Glu Leu Ser Ile Leu Ala Arg Thr Phe Lys Asn Thr Gln Leu Pro Glu
        2260                2265                2270

AGG GCA ATA TTT CAA ATT AAA CAG TAC AAT TCA GTT AGC TGT GGA GTC      6864
Arg Ala Ile Phe Gln Ile Lys Gln Tyr Asn Ser Val Ser Cys Gly Val
        2275                2280                2285

TCT GAG TGG CAG CTG GAA GAA GCA CAA GTA TTC TGG GCA AAA AAG GAG      6912
Ser Glu Trp Gln Leu Glu Glu Ala Gln Val Phe Trp Ala Lys Lys Glu
        2290                2295                2300

CAG AGT CTT GCC CTG AGT ATT CTC AAG CAA ATG ATC AAG AAG TTG GAT      6960
Gln Ser Leu Ala Leu Ser Ile Leu Lys Gln Met Ile Lys Lys Leu Asp
2305                2310                2315                2320

GCC AGC TGT GCA GCG AAC AAT CCC AGC CTA AAA CTT ACA TAC ACA GAA      7008
Ala Ser Cys Ala Ala Asn Asn Pro Ser Leu Lys Leu Thr Tyr Thr Glu
            2325                2330                2335

TGT CTG AGG GTT TGT GGC AAC TGG TTA GCA GAA ACG TGC TTA GAA AAT      7056
Cys Leu Arg Val Cys Gly Asn Trp Leu Ala Glu Thr Cys Leu Glu Asn
            2340                2345                2350

CCT GCG GTC ATC ATG CAG ACC TAT CTA GAA AAG GCA GTA GAA GTT GCT      7104
Pro Ala Val Ile Met Gln Thr Tyr Leu Glu Lys Ala Val Glu Val Ala
        2355                2360                2365

GGA AAT TAT GAT GGA GAA AGT AGT GAT GAG CTA AGA AAT GGA AAA ATG      7152
Gly Asn Tyr Asp Gly Glu Ser Ser Asp Glu Leu Arg Asn Gly Lys Met
        2370                2375                2380

AAG GCA TTT CTC TCA TTA GCC CGG TTT TCA GAT ACT CAA TAC CAA AGA      7200
Lys Ala Phe Leu Ser Leu Ala Arg Phe Ser Asp Thr Gln Tyr Gln Arg
2385                2390                2395                2400

ATT GAA AAC TAC ATG AAA TCA TCG GAA TTT GAA AAC AAG CAA GCT CTC      7248
Ile Glu Asn Tyr Met Lys Ser Ser Glu Phe Glu Asn Lys Gln Ala Leu
            2405                2410                2415

CTG AAA AGA GCC AAA GAG GAA GTA GGT CTC CTT AGG GAA CAT AAA ATT      7296
Leu Lys Arg Ala Lys Glu Glu Val Gly Leu Leu Arg Glu His Lys Ile
            2420                2425                2430

CAG ACA AAC AGA TAC ACA GTA AAG GTT CAG CGA GAG CTG GAG TTG GAT      7344
Gln Thr Asn Arg Tyr Thr Val Lys Val Gln Arg Glu Leu Glu Leu Asp
        2435                2440                2445

GAA TTA GCC CTG CGT GCA CTG AAA GAG GAT CGT AAA CGC TTC TTA TGT      7392
Glu Leu Ala Leu Arg Ala Leu Lys Glu Asp Arg Lys Arg Phe Leu Cys
        2450                2455                2460

AAA GCA GTT GAA AAT TAT ATC AAC TGC TTA TTA AGT GGA GAA GAA CAT      7440
Lys Ala Val Glu Asn Tyr Ile Asn Cys Leu Leu Ser Gly Glu Glu His
2465                2470                2475                2480

GAT ATG TGG GTA TTC CGG CTT TGT TCC CTC TGG CTT GAA AAT TCT GGA      7488
Asp Met Trp Val Phe Arg Leu Cys Ser Leu Trp Leu Glu Asn Ser Gly
            2485                2490                2495

GTT TCT GAA GTC AAT GGC ATG ATG AAG AGA GAC GGA ATG AAG ATT CCA      7536
Val Ser Glu Val Asn Gly Met Met Lys Arg Asp Gly Met Lys Ile Pro
```

-continued

```
              2500                2505                2510
ACA TAT AAA TTT TTG CCT CTT ATG TAC CAA TTG GCT GCT AGA ATG GGG      7584
Thr Tyr Lys Phe Leu Pro Leu Met Tyr Gln Leu Ala Ala Arg Met Gly
        2515                2520                2525

ACC AAG ATG ATG GGA GGC CTA GGA TTT CAT GAA GTC CTC AAT AAT CTA      7632
Thr Lys Met Met Gly Gly Leu Gly Phe His Glu Val Leu Asn Asn Leu
        2530                2535                2540

ATC TCT AGA ATT TCA ATG GAT CAC CCC CAT CAC ACT TTG TTT ATT ATA      7680
Ile Ser Arg Ile Ser Met Asp His Pro His His Thr Leu Phe Ile Ile
2545                2550                2555                2560

CTG GCC TTA GCA AAT GCA AAC AGA GAT GAA TTT CTG ACT AAA CCA GAG      7728
Leu Ala Leu Ala Asn Ala Asn Arg Asp Glu Phe Leu Thr Lys Pro Glu
        2565                2570                2575

GTA GCC AGA AGA AGC AGA ATA ACT AAA AAT GTG CCT AAA CAA AGC TCT      7776
Val Ala Arg Arg Ser Arg Ile Thr Lys Asn Val Pro Lys Gln Ser Ser
        2580                2585                2590

CAG CTT GAT GAG GAT CGA ACA GAG GCT GCA AAT AGA ATA ATA TGT ACT      7824
Gln Leu Asp Glu Asp Arg Thr Glu Ala Ala Asn Arg Ile Ile Cys Thr
        2595                2600                2605

ATC AGA AGT AGG AGA CCT CAG ATG GTC AGA AGT GTT GAG GCA CTT TGT      7872
Ile Arg Ser Arg Arg Pro Gln Met Val Arg Ser Val Glu Ala Leu Cys
        2610                2615                2620

GAT GCT TAT ATT ATA TTA GCA AAC TTA GAT GCC ACT CAG TGG AAG ACT      7920
Asp Ala Tyr Ile Ile Leu Ala Asn Leu Asp Ala Thr Gln Trp Lys Thr
2625                2630                2635                2640

CAG AGA AAA GGC ATA AAT ATT CCA GCA GAC CAG CCA ATT ACT AAA CTT      7968
Gln Arg Lys Gly Ile Asn Ile Pro Ala Asp Gln Pro Ile Thr Lys Leu
        2645                2650                2655

AAG AAT TTA GAA GAT GTT GTT GTC CCT ACT ATG GAA ATT AAG GTG GAC      8016
Lys Asn Leu Glu Asp Val Val Val Pro Thr Met Glu Ile Lys Val Asp
        2660                2665                2670

CAC ACA GGA GAA TAT GGA AAT CTG GTG ACT ATA CAG TCA TTT AAA GCA      8064
His Thr Gly Glu Tyr Gly Asn Leu Val Thr Ile Gln Ser Phe Lys Ala
        2675                2680                2685

GAA TTT CGC TTA GCA GGA GGT GTA AAT TTA CCA AAA ATA ATA GAT TGT      8112
Glu Phe Arg Leu Ala Gly Gly Val Asn Leu Pro Lys Ile Ile Asp Cys
        2690                2695                2700

GTA GGT TCC GAT GGC AAG GAG AGG AGA CAG CTT GTT AAG GGC CGT GAT      8160
Val Gly Ser Asp Gly Lys Glu Arg Arg Gln Leu Val Lys Gly Arg Asp
2705                2710                2715                2720

GAC CTG AGA CAA GAT GCT GTC ATG CAA CAG GTC TTC CAG ATG TGT AAT      8208
Asp Leu Arg Gln Asp Ala Val Met Gln Gln Val Phe Gln Met Cys Asn
        2725                2730                2735

ACA TTA CTG CAG AGA AAC ACG GAA ACT AGG AAG AGG AAA TTA ACT ATC      8256
Thr Leu Leu Gln Arg Asn Thr Glu Thr Arg Lys Arg Lys Leu Thr Ile
        2740                2745                2750

TGT ACT TAT AAG GTG GTT CCC CTC TCT CAG CGA AGT GGT GTT CTT GAA      8304
Cys Thr Tyr Lys Val Val Pro Leu Ser Gln Arg Ser Gly Val Leu Glu
        2755                2760                2765

TGG TGC ACA GGA ACT GTC CCC ATT GGT GAA TTT CTT GTT AAC AAT GAA      8352
Trp Cys Thr Gly Thr Val Pro Ile Gly Glu Phe Leu Val Asn Asn Glu
        2770                2775                2780

GAT GGT GCT CAT AAA AGA TAC AGG CCA AAT GAT TTC AGT GCC TTT CAG      8400
Asp Gly Ala His Lys Arg Tyr Arg Pro Asn Asp Phe Ser Ala Phe Gln
2785                2790                2795                2800

TGC CAA AAG AAA ATG ATG GAG GTG CAA AAA AAG TCT TTT GAA GAG AAA      8448
Cys Gln Lys Lys Met Met Glu Val Gln Lys Lys Ser Phe Glu Glu Lys
        2805                2810                2815

TAT GAA GTC TTC ATG GAT GTT TGC CAA AAT TTT CAA CCA GTT TTC CGT      8496
```

|  |  |  |  |  |  |  |  |  |  |  |  |  |  |  |  |
|---|---|---|---|---|---|---|---|---|---|---|---|---|---|---|---|
| Tyr | Glu | Val | Phe | Met | Asp | Val | Cys | Gln | Asn | Phe | Gln | Pro | Val | Phe | Arg |
|  |  | 2820 |  |  |  | 2825 |  |  |  | 2830 |  |  |  |  |  |

```
TAC TTC TGC ATG GAA AAA TTC TTG GAT CCA GCT ATT TGG TTT GAG AAG      8544
Tyr Phe Cys Met Glu Lys Phe Leu Asp Pro Ala Ile Trp Phe Glu Lys
            2835                2840                2845

CGA TTG GCT TAT ACG CGC AGT GTA GCT ACT TCT TCT ATT GTT GGT TAC      8592
Arg Leu Ala Tyr Thr Arg Ser Val Ala Thr Ser Ser Ile Val Gly Tyr
    2850                2855                2860

ATA CTT GGA CTT GGT GAT AGA CAT GTA CAG AAT ATC TTG ATA AAT GAG      8640
Ile Leu Gly Leu Gly Asp Arg His Val Gln Asn Ile Leu Ile Asn Glu
2865                2870                2875                2880

CAG TCA GCA GAA CTT GTA CAT ATA GAT CTA GGT GTT GCT TTT GAA CAG      8688
Gln Ser Ala Glu Leu Val His Ile Asp Leu Gly Val Ala Phe Glu Gln
                2885                2890                2895

GGC AAA ATC CTT CCT ACT CCT GAG ACA GTT CCT TTT AGA CTC ACC AGA      8736
Gly Lys Ile Leu Pro Thr Pro Glu Thr Val Pro Phe Arg Leu Thr Arg
            2900                2905                2910

GAT ATT GTG GAT GGC ATG GGC ATT ACG GGT GTT GAA GGT GTC TTC AGA      8784
Asp Ile Val Asp Gly Met Gly Ile Thr Gly Val Glu Gly Val Phe Arg
        2915                2920                2925

AGA TGC TGT GAG AAA ACC ATG GAA GTG ATG AGA AAC TCT CAG GAA ACT      8832
Arg Cys Cys Glu Lys Thr Met Glu Val Met Arg Asn Ser Gln Glu Thr
    2930                2935                2940

CTG TTA ACC ATT GTA GAG GTC CTT CTA TAT GAT CCA CTC TTT GAC TGG      8880
Leu Leu Thr Ile Val Glu Val Leu Leu Tyr Asp Pro Leu Phe Asp Trp
2945                2950                2955                2960

ACC ATG AAT CCT TTG AAA GCT TTG TAT TTA CAG CAG AGG CCG GAA GAT      8928
Thr Met Asn Pro Leu Lys Ala Leu Tyr Leu Gln Gln Arg Pro Glu Asp
                2965                2970                2975

GAA ACT GAG CTT CAC CCT ACT CTG AAT GCA GAT GAC CAA GAA TGC AAA      8976
Glu Thr Glu Leu His Pro Thr Leu Asn Ala Asp Asp Gln Glu Cys Lys
            2980                2985                2990

CGA AAT CTC AGT GAT ATT GAC CAG AGT TTC GAC AAA GTA GCT GAA CGT      9024
Arg Asn Leu Ser Asp Ile Asp Gln Ser Phe Asp Lys Val Ala Glu Arg
        2995                3000                3005

GTC TTA ATG AGA CTA CAA GAG AAA CTG AAA GGA GTG GAA GAA GGC ACT      9072
Val Leu Met Arg Leu Gln Glu Lys Leu Lys Gly Val Glu Glu Gly Thr
    3010                3015                3020

GTG CTC AGT GTT GGT GGA CAG GTG AAT TTG CTC ATA CAG CAG GCC ATA      9120
Val Leu Ser Val Gly Gly Gln Val Asn Leu Leu Ile Gln Gln Ala Ile
3025                3030                3035                3040

GAC CCC AAA AAT CTC AGC CGA CTT TTC CCA GGA TGG AAA GCT TGG GTG      9168
Asp Pro Lys Asn Leu Ser Arg Leu Phe Pro Gly Trp Lys Ala Trp Val
                3045                3050                3055

TGATCTTCAG TATATGAATT ACCCTTTC                                        9196
```

(2) INFORMATION FOR SEQ ID NO:2:

(i) SEQUENCE CHARACTERISTICS:
        (A) LENGTH: 3056 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Leu Val Leu Asn Asp Leu Leu Ile Cys Cys Arg Gln Leu Glu
 1               5                  10                  15

His Asp Arg Ala Thr Glu Arg Lys Lys Glu Val Glu Lys Phe Lys Arg
            20                  25                  30
```

-continued

```
Leu Ile Arg Asp Pro Glu Thr Ile Lys His Leu Asp Arg His Ser Asp
         35                  40                  45
Ser Lys Gln Gly Lys Tyr Leu Asn Trp Asp Ala Val Phe Arg Phe Leu
 50                  55                  60
Gln Lys Tyr Ile Gln Lys Glu Thr Glu Cys Leu Arg Ile Ala Lys Pro
 65                  70                  75                  80
Asn Val Ser Ala Ser Thr Gln Ala Ser Arg Gln Lys Lys Met Gln Glu
                 85                  90                  95
Ile Ser Ser Leu Val Lys Tyr Phe Ile Lys Cys Ala Asn Arg Arg Ala
                100                 105                 110
Pro Arg Leu Lys Cys Gln Glu Leu Leu Asn Tyr Ile Met Asp Thr Val
         115                 120                 125
Lys Asp Ser Ser Asn Gly Ala Ile Tyr Gly Ala Asp Cys Ser Asn Ile
 130                 135                 140
Leu Leu Lys Asp Ile Leu Ser Val Arg Lys Tyr Trp Cys Glu Ile Ser
145                 150                 155                 160
Gln Gln Gln Trp Leu Glu Leu Phe Ser Val Tyr Phe Arg Leu Tyr Leu
                165                 170                 175
Lys Pro Ser Gln Asp Val His Arg Val Leu Val Ala Arg Ile Ile His
         180                 185                 190
Ala Val Thr Lys Gly Cys Cys Ser Gln Thr Asp Gly Leu Asn Ser Lys
         195                 200                 205
Phe Leu Asp Phe Phe Ser Lys Ala Ile Gln Cys Ala Arg Gln Glu Lys
 210                 215                 220
Ser Ser Ser Gly Leu Asn His Ile Leu Ala Ala Leu Thr Ile Phe Leu
225                 230                 235                 240
Lys Thr Leu Ala Val Asn Phe Arg Ile Arg Val Cys Glu Leu Gly Asp
                245                 250                 255
Glu Ile Leu Pro Thr Leu Leu Tyr Ile Trp Thr Gln His Arg Leu Asn
         260                 265                 270
Asp Ser Leu Lys Glu Val Ile Ile Glu Leu Phe Gln Leu Gln Ile Tyr
         275                 280                 285
Ile His His Pro Lys Gly Ala Lys Thr Gln Glu Lys Gly Ala Tyr Glu
 290                 295                 300
Ser Thr Lys Trp Arg Ser Ile Leu Tyr Asn Leu Tyr Asp Leu Leu Val
305                 310                 315                 320
Asn Glu Ile Ser His Ile Gly Ser Arg Gly Lys Tyr Ser Ser Gly Phe
                325                 330                 335
Arg Asn Ile Ala Val Lys Glu Asn Leu Ile Glu Leu Met Ala Asp Ile
         340                 345                 350
Cys His Gln Val Phe Asn Glu Asp Thr Arg Ser Leu Glu Ile Ser Gln
         355                 360                 365
Ser Tyr Thr Thr Thr Gln Arg Glu Ser Ser Asp Tyr Ser Val Pro Cys
 370                 375                 380
Lys Arg Lys Lys Ile Glu Leu Gly Trp Glu Val Ile Lys Asp His Leu
385                 390                 395                 400
Gln Lys Ser Gln Asn Asp Phe Asp Leu Val Pro Trp Leu Gln Ile Ala
                405                 410                 415
Thr Gln Leu Ile Ser Lys Tyr Pro Ala Ser Leu Pro Asn Cys Glu Leu
         420                 425                 430
Ser Pro Leu Leu Met Ile Leu Ser Gln Leu Leu Pro Gln Gln Arg His
         435                 440                 445
Gly Glu Arg Thr Pro Tyr Val Leu Arg Cys Leu Thr Glu Val Ala Leu
```

```
                450                 455                 460
Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
                500                 505                 510

Gln Gly Ser Leu Val Glu Val Asp Arg Glu Phe Trp Lys Leu Phe Thr
                515                 520                 525

Gly Ser Ala Cys Arg Pro Ser Cys Pro Ala Val Cys Cys Leu Thr Leu
                530                 535                 540

Ala Leu Thr Thr Ser Ile Val Pro Gly Ala Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
                580                 585                 590

Thr Glu Val Pro Pro Ile Leu His Ser Asn Phe Pro His Leu Val Leu
                595                 600                 605

Glu Lys Ile Leu Val Ser Leu Thr Met Lys Asn Cys Lys Ala Ala Met
                610                 615                 620

Asn Phe Phe Gln Ser Val Pro Glu Cys Glu His His Gln Lys Asp Lys
625                 630                 635                 640

Glu Glu Leu Ser Phe Ser Glu Val Glu Leu Phe Leu Gln Thr Thr
                645                 650                 655

Phe Asp Lys Met Asp Phe Leu Thr Ile Val Arg Glu Cys Gly Ile Glu
                660                 665                 670

Lys His Gln Ser Ser Ile Gly Phe Ser Val His Gln Asn Leu Lys Glu
                675                 680                 685

Ser Leu Asp Arg Cys Leu Leu Gly Leu Ser Glu Gln Leu Leu Asn Asn
                690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Asn Ser Leu
                740                 745                 750

Met Gln Cys Ala Gly Glu Ser Ile Thr Leu Phe Lys Asn Lys Thr Asn
                755                 760                 765

Glu Glu Phe Arg Ile Gly Ser Leu Arg Asn Met Met Gln Leu Cys Thr
                770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
                820                 825                 830

Gly Glu Val Glu Ser Met Glu Asp Asp Thr Asn Gly Asn Leu Met Glu
                835                 840                 845

Val Glu Asp Gln Ser Ser Met Asn Leu Phe Asn Asp Tyr Pro Asp Ser
                850                 855                 860

Ser Val Ser Asp Ala Asn Glu Pro Gly Glu Ser Gln Ser Thr Ile Gly
865                 870                 875                 880
```

```
Ala Ile Asn Pro Leu Ala Glu Glu Tyr Leu Ser Lys Gln Asp Leu Leu
            885                 890                 895
Phe Leu Asp Met Leu Lys Phe Leu Cys Leu Cys Val Thr Thr Ala Gln
            900                 905                 910
Thr Asn Thr Val Ser Phe Arg Ala Ala Asp Ile Arg Arg Lys Leu Leu
            915                 920                 925
Met Leu Ile Asp Ser Ser Thr Leu Glu Pro Thr Lys Ser Leu His Leu
            930                 935                 940
His Met Tyr Leu Met Leu Leu Lys Glu Leu Pro Gly Glu Glu Tyr Pro
945                 950                 955                 960
Leu Pro Met Glu Asp Val Leu Glu Leu Leu Lys Pro Leu Ser Asn Val
            965                 970                 975
Cys Ser Leu Tyr Arg Arg Asp Gln Asp Val Cys Lys Thr Ile Leu Asn
            980                 985                 990
His Val Leu His Val Val Lys Asn Leu Gly Gln Ser Asn Met Asp Ser
            995                 1000                1005
Glu Asn Thr Arg Asp Ala Gln Gly Gln Phe Leu Thr Val Ile Gly Ala
            1010                1015                1020
Phe Trp His Leu Thr Lys Glu Arg Lys Tyr Ile Phe Ser Val Arg Met
1025                1030                1035                1040
Ala Leu Val Asn Cys Leu Lys Thr Leu Leu Glu Ala Asp Pro Tyr Ser
            1045                1050                1055
Lys Trp Ala Ile Leu Asn Val Met Gly Lys Asp Phe Pro Val Asn Glu
            1060                1065                1070
Val Phe Thr Gln Phe Leu Ala Asp Asn His His Gln Val Arg Met Leu
            1075                1080                1085
Ala Ala Glu Ser Ile Asn Arg Leu Phe Gln Asp Thr Lys Gly Asp Ser
            1090                1095                1100
Ser Arg Leu Leu Lys Ala Leu Pro Leu Lys Leu Gln Gln Thr Ala Phe
1105                1110                1115                1120
Glu Asn Ala Tyr Leu Lys Ala Gln Glu Gly Met Arg Glu Met Ser His
            1125                1130                1135
Ser Ala Glu Asn Pro Glu Thr Leu Asp Glu Ile Tyr Asn Arg Lys Ser
            1140                1145                1150
Val Leu Leu Thr Leu Ile Ala Val Val Leu Ser Cys Ser Pro Ile Cys
            1155                1160                1165
Glu Lys Gln Ala Leu Phe Ala Leu Cys Lys Ser Val Lys Glu Asn Gly
            1170                1175                1180
Leu Glu Pro His Leu Val Lys Lys Val Leu Glu Lys Val Ser Glu Thr
1185                1190                1195                1200
Phe Gly Tyr Arg Arg Leu Glu Asp Phe Met Ala Ser His Leu Asp Tyr
            1205                1210                1215
Leu Val Leu Glu Trp Leu Asn Leu Gln Asp Thr Glu Tyr Asn Leu Ser
            1220                1225                1230
Ser Phe Pro Phe Ile Leu Leu Asn Tyr Thr Asn Ile Glu Asp Phe Tyr
            1235                1240                1245
Arg Ser Cys Tyr Lys Val Leu Ile Pro His Leu Val Ile Arg Ser His
            1250                1255                1260
Phe Asp Glu Val Lys Ser Ile Ala Asn Gln Ile Gln Glu Asp Trp Lys
1265                1270                1275                1280
Ser Leu Leu Thr Asp Cys Phe Pro Lys Ile Leu Val Asn Ile Leu Pro
            1285                1290                1295
```

```
Tyr Phe Ala Tyr Glu Gly Thr Arg Asp Ser Gly Met Ala Gln Gln Arg
            1300                1305                1310

Glu Thr Ala Thr Lys Val Tyr Asp Met Leu Lys Ser Glu Asn Leu Leu
            1315                1320                1325

Gly Lys Gln Ile Asp His Leu Phe Ile Ser Asn Leu Pro Glu Ile Val
            1330                1335                1340

Val Glu Leu Leu Met Thr Leu His Glu Pro Ala Asn Ser Ser Ala Ser
1345                1350                1355                1360

Gln Ser Thr Asp Leu Cys Asp Phe Ser Gly Asp Leu Asp Pro Ala Pro
                1365                1370                1375

Asn Pro Pro His Phe Pro Ser His Val Ile Lys Ala Thr Phe Ala Tyr
                1380                1385                1390

Ile Ser Asn Cys His Lys Thr Lys Leu Lys Ser Ile Leu Glu Ile Leu
            1395                1400                1405

Ser Lys Ser Pro Asp Ser Tyr Gln Lys Ile Leu Leu Ala Ile Cys Glu
            1410                1415                1420

Gln Ala Ala Glu Thr Asn Asn Val Tyr Lys Lys His Arg Ile Leu Lys
1425                1430                1435                1440

Ile Tyr His Leu Phe Val Ser Leu Leu Leu Lys Asp Ile Lys Ser Gly
                1445                1450                1455

Leu Gly Gly Ala Trp Ala Phe Val Leu Arg Asp Val Ile Tyr Thr Leu
            1460                1465                1470

Ile His Tyr Ile Asn Gln Arg Pro Ser Cys Ile Met Asp Val Ser Leu
            1475                1480                1485

Arg Ser Phe Ser Leu Cys Cys Asp Leu Leu Ser Gln Val Cys Gln Thr
            1490                1495                1500

Ala Val Thr Tyr Cys Lys Asp Ala Leu Glu Asn His Leu His Val Ile
1505                1510                1515                1520

Val Gly Thr Leu Ile Pro Leu Val Tyr Glu Gln Val Glu Val Gln Lys
                1525                1530                1535

Gln Val Leu Asp Leu Leu Lys Tyr Leu Val Ile Asp Asn Lys Asp Asn
                1540                1545                1550

Glu Asn Leu Tyr Ile Thr Ile Lys Leu Leu Asp Pro Phe Pro Asp His
            1555                1560                1565

Val Val Phe Lys Asp Leu Arg Ile Thr Gln Gln Lys Ile Lys Tyr Ser
            1570                1575                1580

Arg Gly Pro Phe Ser Leu Leu Glu Glu Ile Asn His Phe Leu Ser Val
1585                1590                1595                1600

Ser Val Tyr Asp Ala Leu Pro Leu Thr Arg Leu Glu Gly Leu Lys Asp
                1605                1610                1615

Leu Arg Arg Gln Leu Glu Leu His Lys Asp Gln Met Val Asp Ile Met
                1620                1625                1630

Arg Ala Ser Gln Asp Asn Pro Gln Asp Gly Ile Met Val Lys Leu Val
            1635                1640                1645

Val Asn Leu Leu Gln Leu Ser Lys Met Ala Ile Asn His Thr Gly Glu
            1650                1655                1660

Lys Glu Val Leu Glu Ala Val Gly Ser Cys Leu Gly Glu Val Gly Pro
1665                1670                1675                1680

Ile Asp Phe Ser Thr Ile Ala Ile Gln His Ser Lys Asp Ala Ser Tyr
                1685                1690                1695

Thr Lys Ala Leu Lys Leu Phe Glu Asp Lys Glu Leu Gln Trp Thr Phe
                1700                1705                1710

Ile Met Leu Thr Tyr Leu Asn Asn Thr Leu Val Glu Asp Cys Val Lys
```

-continued

```
                1715                1720                   1725
Val Arg Ser Ala Ala Val Thr Cys Leu Lys Asn Ile Leu Ala Thr Lys
            1730                1735                1740
Thr Gly His Ser Phe Trp Glu Ile Tyr Lys Met Thr Thr Asp Pro Met
1745                1750                1755                1760
Leu Ala Tyr Leu Gln Pro Phe Arg Thr Ser Arg Lys Lys Phe Leu Glu
                1765                1770                1775
Val Pro Arg Phe Asp Lys Glu Asn Pro Phe Glu Gly Leu Asp Asp Ile
            1780                1785                1790
Asn Leu Trp Ile Pro Leu Ser Glu Asn His Asp Ile Trp Ile Lys Thr
                1795                1800                1805
Leu Thr Cys Ala Phe Leu Asp Ser Gly Gly Thr Lys Cys Glu Ile Leu
            1810                1815                1820
Gln Leu Leu Lys Pro Met Cys Glu Val Lys Thr Asp Phe Cys Gln Thr
1825                1830                1835                1840
Val Leu Pro Tyr Leu Ile His Asp Ile Leu Leu Gln Asp Thr Asn Glu
                1845                1850                1855
Ser Trp Arg Asn Leu Leu Ser Thr His Val Gln Gly Phe Phe Thr Ser
            1860                1865                1870
Cys Leu Arg His Phe Ser Gln Thr Ser Arg Ser Thr Thr Pro Ala Asn
            1875                1880                1885
Leu Asp Ser Glu Ser Glu His Phe Phe Arg Cys Cys Leu Asp Lys Lys
            1890                1895                1900
Ser Gln Arg Thr Met Leu Ala Val Val Asp Tyr Met Arg Arg Gln Lys
1905                1910                1915                1920
Arg Pro Ser Ser Gly Thr Ile Phe Asn Asp Ala Phe Trp Leu Asp Leu
                1925                1930                1935
Asn Tyr Leu Glu Val Ala Lys Val Ala Gln Ser Cys Ala Ala His Phe
            1940                1945                1950
Thr Ala Leu Leu Tyr Ala Glu Ile Tyr Ala Asp Lys Lys Ser Met Asp
            1955                1960                1965
Asp Gln Glu Lys Arg Ser Leu Ala Phe Glu Glu Gly Ser Gln Ser Thr
            1970                1975                1980
Thr Ile Ser Ser Leu Ser Glu Lys Ser Lys Glu Glu Thr Gly Ile Ser
1985                1990                1995                2000
Leu Gln Asp Leu Leu Leu Glu Ile Tyr Arg Ser Ile Gly Glu Pro Asp
                2005                2010                2015
Ser Leu Tyr Gly Cys Gly Gly Gly Lys Met Leu Gln Pro Ile Thr Arg
                2020                2025                2030
Leu Arg Thr Tyr Glu His Glu Ala Met Trp Gly Lys Ala Leu Val Thr
            2035                2040                2045
Tyr Asp Leu Glu Thr Ala Ile Pro Ser Ser Thr Arg Gln Ala Gly Ile
            2050                2055                2060
Ile Gln Ala Leu Gln Asn Leu Gly Leu Cys His Ile Leu Ser Val Tyr
2065                2070                2075                2080
Leu Lys Gly Leu Asp Tyr Glu Asn Lys Asp Trp Cys Pro Glu Leu Glu
                2085                2090                2095
Glu Leu His Tyr Gln Ala Ala Trp Arg Asn Met Gln Trp Asp His Cys
                2100                2105                2110
Thr Ser Val Ser Lys Glu Val Glu Gly Thr Ser Tyr His Glu Ser Leu
            2115                2120                2125
Tyr Asn Ala Leu Gln Ser Leu Arg Asp Arg Glu Phe Ser Thr Phe Tyr
            2130                2135                2140
```

```
Glu Ser Leu Lys Tyr Ala Arg Val Lys Glu Val Glu Met Cys Lys
2145                2150                2155                2160

Arg Ser Leu Glu Ser Val Tyr Ser Leu Tyr Pro Thr Leu Ser Arg Leu
            2165                2170                2175

Gln Ala Ile Gly Glu Leu Glu Ser Ile Gly Glu Leu Phe Ser Arg Ser
        2180                2185                2190

Val Thr His Arg Gln Leu Ser Glu Val Tyr Ile Lys Trp Gln Lys His
            2195                2200                2205

Ser Gln Leu Leu Lys Asp Ser Asp Phe Ser Phe Gln Glu Pro Ile Met
        2210                2215                2220

Ala Leu Arg Thr Val Ile Leu Glu Ile Leu Met Glu Lys Glu Met Asp
2225                2230                2235                2240

Asn Ser Gln Arg Glu Cys Ile Lys Asp Ile Leu Thr Lys His Leu Val
            2245                2250                2255

Glu Leu Ser Ile Leu Ala Arg Thr Phe Lys Asn Thr Gln Leu Pro Glu
        2260                2265                2270

Arg Ala Ile Phe Gln Ile Lys Gln Tyr Asn Ser Val Ser Cys Gly Val
            2275                2280                2285

Ser Glu Trp Gln Leu Glu Glu Ala Gln Val Phe Trp Ala Lys Lys Glu
        2290                2295                2300

Gln Ser Leu Ala Leu Ser Ile Leu Lys Gln Met Ile Lys Lys Leu Asp
2305                2310                2315                2320

Ala Ser Cys Ala Ala Asn Asn Pro Ser Leu Lys Leu Thr Tyr Thr Glu
            2325                2330                2335

Cys Leu Arg Val Cys Gly Asn Trp Leu Ala Glu Thr Cys Leu Glu Asn
        2340                2345                2350

Pro Ala Val Ile Met Gln Thr Tyr Leu Glu Lys Ala Val Glu Val Ala
            2355                2360                2365

Gly Asn Tyr Asp Gly Glu Ser Ser Asp Glu Leu Arg Asn Gly Lys Met
        2370                2375                2380

Lys Ala Phe Leu Ser Leu Ala Arg Phe Ser Asp Thr Gln Tyr Gln Arg
2385                2390                2395                2400

Ile Glu Asn Tyr Met Lys Ser Ser Glu Phe Glu Asn Lys Gln Ala Leu
            2405                2410                2415

Leu Lys Arg Ala Lys Glu Glu Val Gly Leu Leu Arg Glu His Lys Ile
        2420                2425                2430

Gln Thr Asn Arg Tyr Thr Val Lys Val Gln Arg Glu Leu Glu Leu Asp
        2435                2440                2445

Glu Leu Ala Leu Arg Ala Leu Lys Glu Asp Arg Lys Arg Phe Leu Cys
2450                2455                2460

Lys Ala Val Glu Asn Tyr Ile Asn Cys Leu Leu Ser Gly Glu Glu His
2465                2470                2475                2480

Asp Met Trp Val Phe Arg Leu Cys Ser Leu Trp Leu Glu Asn Ser Gly
            2485                2490                2495

Val Ser Glu Val Asn Gly Met Met Lys Arg Asp Gly Met Lys Ile Pro
            2500                2505                2510

Thr Tyr Lys Phe Leu Pro Leu Met Tyr Gln Leu Ala Ala Arg Met Gly
            2515                2520                2525

Thr Lys Met Met Gly Gly Leu Gly Phe His Glu Val Leu Asn Asn Leu
        2530                2535                2540

Ile Ser Arg Ile Ser Met Asp His Pro His His Thr Leu Phe Ile Ile
2545                2550                2555                2560
```

-continued

```
Leu Ala Leu Ala Asn Ala Asn Arg Asp Glu Phe Leu Thr Lys Pro Glu
                2565                2570                2575
Val Ala Arg Arg Ser Arg Ile Thr Lys Asn Val Pro Lys Gln Ser Ser
            2580                2585                2590
Gln Leu Asp Glu Asp Arg Thr Glu Ala Ala Asn Arg Ile Ile Cys Thr
        2595                2600                2605
Ile Arg Ser Arg Arg Pro Gln Met Val Arg Ser Val Glu Ala Leu Cys
    2610                2615                2620
Asp Ala Tyr Ile Ile Leu Ala Asn Leu Asp Ala Thr Gln Trp Lys Thr
2625                2630                2635                2640
Gln Arg Lys Gly Ile Asn Ile Pro Ala Asp Gln Pro Ile Thr Lys Leu
            2645                2650                2655
Lys Asn Leu Glu Asp Val Val Pro Thr Met Glu Ile Lys Val Asp
            2660                2665                2670
His Thr Gly Glu Tyr Gly Asn Leu Val Thr Ile Gln Ser Phe Lys Ala
        2675                2680                2685
Glu Phe Arg Leu Ala Gly Gly Val Asn Leu Pro Lys Ile Ile Asp Cys
    2690                2695                2700
Val Gly Ser Asp Gly Lys Glu Arg Arg Gln Leu Val Lys Gly Arg Asp
2705                2710                2715                2720
Asp Leu Arg Gln Asp Ala Val Met Gln Gln Val Phe Gln Met Cys Asn
            2725                2730                2735
Thr Leu Leu Gln Arg Asn Thr Glu Thr Arg Lys Arg Lys Leu Thr Ile
        2740                2745                2750
Cys Thr Tyr Lys Val Val Pro Leu Ser Gln Arg Ser Gly Val Leu Glu
    2755                2760                2765
Trp Cys Thr Gly Thr Val Pro Ile Gly Glu Phe Leu Val Asn Asn Glu
    2770                2775                2780
Asp Gly Ala His Lys Arg Tyr Arg Pro Asn Asp Phe Ser Ala Phe Gln
2785                2790                2795                2800
Cys Gln Lys Lys Met Met Glu Val Gln Lys Lys Ser Phe Glu Glu Lys
            2805                2810                2815
Tyr Glu Val Phe Met Asp Val Cys Gln Asn Phe Gln Pro Val Phe Arg
        2820                2825                2830
Tyr Phe Cys Met Glu Lys Phe Leu Asp Pro Ala Ile Trp Phe Glu Lys
    2835                2840                2845
Arg Leu Ala Tyr Thr Arg Ser Val Ala Thr Ser Ser Ile Val Gly Tyr
    2850                2855                2860
Ile Leu Gly Leu Gly Asp Arg His Val Gln Asn Ile Leu Ile Asn Glu
2865                2870                2875                2880
Gln Ser Ala Glu Leu Val His Ile Asp Leu Gly Val Ala Phe Glu Gln
            2885                2890                2895
Gly Lys Ile Leu Pro Thr Pro Glu Thr Val Pro Phe Arg Leu Thr Arg
        2900                2905                2910
Asp Ile Val Asp Gly Met Gly Ile Thr Gly Val Glu Gly Val Phe Arg
    2915                2920                2925
Arg Cys Cys Glu Lys Thr Met Glu Val Met Arg Asn Ser Gln Glu Thr
2930                2935                2940
Leu Leu Thr Ile Val Glu Val Leu Leu Tyr Asp Pro Leu Phe Asp Trp
2945                2950                2955                2960
Thr Met Asn Pro Leu Lys Ala Leu Tyr Leu Gln Gln Arg Pro Glu Asp
            2965                2970                2975
Glu Thr Glu Leu His Pro Thr Leu Asn Ala Asp Asp Gln Glu Cys Lys
```

```
                    2980            2985            2990
Arg Asn Leu Ser Asp Ile Asp Gln Ser Phe Asp Lys Val Ala Glu Arg
            2995            3000            3005

Val Leu Met Arg Leu Gln Glu Lys Leu Lys Gly Val Glu Glu Gly Thr
        3010            3015            3020

Val Leu Ser Val Gly Gly Gln Val Asn Leu Leu Ile Gln Gln Ala Ile
3025            3030            3035            3040

Asp Pro Lys Asn Leu Ser Arg Leu Phe Pro Gly Trp Lys Ala Trp Val
                3045            3050            3055
```

PREDISPOSITION TO BREAST CANCER BY MUTATIONS AT THE ATAXIA-TELANGIECTASIA GENETIC LOCUS

CROSS REFERENCE TO RELATED APPLICATION

The present application is related to provisional patent application Serial No. 60/032,435, filed Dec. 3, 1996.

This invention was made with Government support under Grant Nos. CA 14235 and CA 50489 awarded by the National Cancer Institute, National Institutes of Health, Bethesda, Md. The United States Government has certain rights in the invention.

BACKGROUND OF THE INVENTION

The present invention relates generally to the field of human genetics. Specifically, the present invention relates to the discovery that some alleles of the A-T gene cause susceptibility to cancer, in particular breast cancer. More specifically, the present invention relates to germline mutations in the A-T gene and their use in the diagnosis of predisposition to breast cancer. The invention further relates to somatic mutations in the A-T gene in human breast cancer and their use in the diagnosis and prognosis of human breast cancer.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Breast cancer is a frequent cancer; there are approximately 183,00 new cases and 46,000 deaths from this cancer each year in the United States. It is the second most common cancer among women today, ranking only behind lung cancer. It has been estimated that the lifetime risk for a woman to develop breast cancer is about 1 in 9, although this figure must be interpreted with caution because not every women lives to age 100.

Breast cancer is treated by surgery, radiation therapy, and chemotherapy. New approaches to treatment have improved the survival of women with diagnosed breast cancer. Still, the most reliable approach to reducing mortality from this cancer is to detect it so early that treatment is more effective. It is well established that screening women by mammography beginning at age 50 leads to a substantial reduction in mortality from this cancer.

The concept that women in certain families were more likely to develop breast cancer than women in other families was noted in antiquity, observed several times in the ninteenth century, and established by family studies in the twentieth century. The observation of familial disposition to breast cancer had modest practical consequences because nothing could be done to decrease the risk of breast cancer for women in high risk families and there was no evidence that knowledge about this problem improved survival. Indeed, one could make a case that the awareness of familial predisposition led primarily to increased anxiety while having limited practical benefit.

In general, there are more cases of breast cancer among first and second degree relatives of breast cancer patients than would be expected according to the incidence of breast cancer in the general population. In a minority of families, the incidence of female breast cancer is so high that the pattern appears to follow a Mendelian autosomal dominent pattern of inheritance. Two genes, BRCA1 and BRCA2, have been shown responsible for the breast cancers in about two-thirds of families in which there are four or more cases of breast cancer. These genes have each been cloned and sequenced. A commercial laboratory, Myriad Genetics, now offers to test individuals to see if they carry BRCA1 or BRCA2, based on sequencing of the DNA from the individuals who are tested. Such testing will be valuable to those women—probably less than 1% of the population—who come from families in which the density of breast cancer is high.

The ataxia-telangiectasia (A-T) gene represents another approach to identifying a gene responsible for some breast cancers. This gene was first recognized because it causes a distinctive autosomal recessive syndrome characterized by cerebellar ataxia and oculocutaneous telangiectasia in children who have two copies of this gene (Swift, 1993). A great deal has been learned about the clinical features and laboratory findings in A-T since its description in the late 1950s. One of the most important facts to emerge was that patients with A-T (who will be called A-T homozygotes) developed cancer at a rate approximately 100-fold greater than children of the same age who do not have A-T (Morrell et al., 1986). It also became evident that the A-T gene makes homozygous patients and their cells many-fold more sensitive to the harmful effects of ionizing radiation. Lymphoid cancers predominate in childhood, while epithelial cancers including breast cancer are seen in adolescent and young adult A-T patients (Swift et al., 1990b).

Still, A-T homozygotes are rare and this gene might be of only theoretical interest except for the series of studies that suggested and now have confirmed that A-T heterozygotes, who constitute approximately 1.4% of the population, are also predisposed to cancer. The first evidence for this came from a study in the early 1970s in which it was shown that the cancer mortality in A-T blood relatives exceeded that of spouse controls in the same families by a statistically significant amount (Swift et al., 1976). This hypothesis was confirmed further by the retrospective analysis of 110 Caucasian A-T families in the United States in which there was a highly significant excess of cancer in the blood relatives when the incidence was compared to that in spouse controls. This study, published in 1987, provided the first evidence that the A-T gene predisposed to breast cancer. (Swift et al., 1987) Further support for the hypothesis was provided by a large scale prospective study of cancer incidence in A-T blood relatives and spouse controls published in 1991 (Swift et al., 1991), and by other smaller studies including two independent studies in Europe (Morrell et al., 1990; Peppard et al., 1988; Borresen et al., 1990).

The interpretation of these previous studies is limited by the facts that not all A-T blood relatives carry the A-T gene and by the inevitable question of how well the spouse controls are matched to the blood relatives. Though the study methods were standard, these limitations on interpretation remained. Further, findings from these earlier studies were characterized by several scientists as "a controversial suggestion," (Kasten, 1995) "a possibility," (Savitsky et al., 1995; Collins, 1996) or, "just a hypothesis" (Boice, 1995).

Thus, it is important to confirm that the A-T gene is associated with breast cancer using the best available genetic methods and identifying mutations in the A-T gene in families with breast cancer.

SUMMARY OF THE INVENTION

The present invention relates generally to the field of human genetics. Specifically, the present invention relates to the discovery that some alleles of the A-T gene cause susceptibility to cancer, in particular breast cancer. More specifically, the present invention relates to germline mutations in the A-T gene and their use in the diagnosis of predisposition to breast cancer. The invention further relates to somatic mutations in the A-T gene in human breast cancer and their use in the diagnosis and prognosis of human breast cancer.

In accordance with the present invention, the hypothesis that A-T heterozygotes are predisposed to breast cancer has now been confirmed with unassailable rigor by collecting a group of female blood relatives with breast cancer in A-T families and testing DNA from each of these individuals to determine which of them carried the A-T gene. The method utilized highly polymorphic, tightly linked flanking markers (Gatti et al., 1994) and the index-test method (Swift et al., 1990a).

In addition, the association of the A-T gene with breast cancer is conclusively established by the identification of specific germline mutations in the A-T gene in families with breast cancer.

DETAILED DESCRIPTION OF THE INVENTION

The present invention relates generally to the field of human genetics. Specifically, the present invention relates to the discovery that some alleles of the A-T gene cause susceptibility to cancer, in particular breast cancer. More specifically, the present invention relates to germline mutations in the A-T gene and their use in the diagnosis of predisposition to breast cancer. The invention further relates to somatic mutations in the A-T gene in human breast cancer and their use in the diagnosis and prognosis of human breast cancer.

In accordance with the present invention, the hypothesis that A-T heterozygotes are predisposed to breast cancer has now been confirmed with unassailable rigor by collecting a group of female blood relatives with breast cancer in A-T families and testing DNA from each of these individuals to determine which of them carried the A-T gene. The method utilized highly polymorphic, tightly linked flanking markers (Gatti et al., 1994) and the index-test method (Swift et al., 1990a).

In addition, the association of the A-T gene with breast cancer is conclusively established by the identification of specific germline mutations in the A-T gene in families with breast cancer.

Briefly, the hypothesis that female heterozygous carriers of the A-T gene are predisposed to breast cancer has now been established as described further below. In this test of the hypothesis, carriers of the A-T gene were identified by tracing the gene in families of A-T homozygous probands through tightly linked DNA markers. This is just one of the ways in which A-T heterozygotes can be identified. Indeed, in these carriers we have directly shown that they carry an A-T mutation in two of them, as described below.

More specifically, the hypothesis that A-T heterozygotes are predisposed to breast cancer was tested by the unbiased statistically powerful index-test method based on molecular genotyping. The A-T gene carrier status of 775 blood relatives in 99 A-T families was determined by tracing the A-T gene in each family through tightly linked flanking DNA markers. There were 33 women with breast cancer who could be genotyped; 25 of these were A-T heterozygotes, compared to 14.9 expected (odds ratio 3.8; 95% confidence limits 1.7–8.4; one-sided P=0.0001). This demonstrates that the A-T gene predisposes heterozygotes to breast cancer. For the 21 breast cancers with onset before age 60, the odds ratio was 2.9 (1.1–7.6; P=0.009) and for the 12 cases with onset at age 60 or older, the odds ratio was 6.4 (1.4–28.8; P=0.002). Thus the breast cancer risk for A-T heterozygous women is not limited to young women but appears even higher at older ages. Of all breast cancers in the United States, 6.6% may occur in women who are A-T heterozygotes. This proportion is several-fold greater than the estimated proportion of carriers of BRCA1 mutations in breast cancer cases with onset at any age.

These new findings demonstrate that a test that reliably identifies heterozygous carriers of the A-T gene identifies individuals whose risk of breast cancer is substantially greater than the risk of non-carriers or the general population. The most efficient and least costly way to identify carriers of this gene may vary from situation to situation, according to the prior art. In one embodiment of the present invention, the least expensive, reliable way to identify gene carriers in families in which the A-T gene is known to be segregating is through tightly linked flanking markers, as in Examples 1 and 2 below.

In a second embodiment of the present invention, this predisposition to female breast cancer in the general population can be detected at present through testing an individual's DNA for mutations at the A-T gene locus. Any reliable laboratory or clinical test that will determine who carries the A-T gene will, according to the use proposed in this patent, be suitable for testing for cancer predisposition.

As an example of the second embodiment, heteroduplex analysis of two of the heterozygous carriers with breast cancer reported in the attached manuscript was used to identify two mutations. For heteroduplex analysis each exon of the A-T gene is amplified by the polymerase chain reaction (PCR) using as template genomic DNA from the test subject. The PCR product is then run on an MDE gel which detects heteroduplexes due to differences between the PCR products from the subject's two chromosomes. If there are no differences, then only a single band is seen and there is no sequence variation in that exon in that subject. When an additional band is seen, the PCR products are cloned so that DNA from each chromosome can be sequenced. The mutation is verified by comparison of the variant sequence to the known sequence of that exon in the A-T gene (Platzer et al., 1997). Further confirmation of the mutation is obtained by sequencing the same exon in close relatives of the subject.

The identification of these mutations conclusively confirms the involvement of the A-T gene in breast cancer. Specifically, one mutation is the nucleotide change ATC→TGAT at base 3245, codon 1082 in exon 24. A second mutation was a deletion of 150 basepairs beginning at nucleotide 8269 of codon 2757, leading to the deletion of exon 59. The first mutation predicts a truncation of the protein and the second predicts a deletion of 50 amino acids. These mutations and those noted herein are numbered with respect to the coding sequence of the A-T gene.

Alternatively, each exon of the A-T gene is amplified by PCR using primers based on the known sequence. The amplified exons are then sequenced using automated sequencers. In this manner, the exons of the A-T gene from families with breast cancer are sequenced until a mutation is found. The mutation is then confirmed in individual with breast cancer. Using this technique, an additional four mutations have been identified. One of these mutations is the deletion of 5 nucleotides beginning at nucleotide 2689 of exon 20. A second mutation is the deletion of AA beginning at nucleotide 1402 of exon 12. A third mutation is the deletion of GAAA beginning at nucleotide 1027 in exon 10. A fourth is the nucleotide change TTT→C at nucleotide 9003 in exon 65.

Also provided by the present invention are methods of detecting a polynucleotide comprising a portion of the A-T locus or its expression product in an analyte. Such methods may further comprise the step of amplifying the portion of the A-T locus, and may further include a step of providing a set of polynucleotides which are primers for amplification of said portion of the A-T locus. The method is useful for either diagnosis of the predisposition to cancer or the diagnosis or prognosis of cancer.

It is a discovery of the present invention that mutations in the A-T locus in the germline are indicative of a predisposition to breast cancer cancer. Finally, it is a discovery of the present invention that somatic mutations in the A-T locus are also associated with breast cancer, which represents an indicator of this cancer or of the prognosis of this cancer. The mutational events of the A-T locus can involve deletions, insertions and point mutations within the coding sequence and the non-coding sequence.

According to the diagnostic and prognostic method of the present invention, alteration of the wild-type A-T locus is detected. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. The finding of A-T mutations thus provides both diagnostic and prognostic information. An A-T allele which is not deleted (e.g., found on the sister chromosome to a chromosome carrying an A-T deletion) can be screened for other mutations, such as insertions, small deletions, and point mutations. It is believed that many mutations found in tumor tissues will be those leading to decreased expression of the A-T gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the A-T gene product, or to a decrease in mRNA stability or translation efficiency.

Useful diagnostic techniques include, but are not limited to direct DNA sequencing, PFGE analysis, allele-specific oligonucleotide (ASO), dot blot analysis and denaturing gradient el electrophoresis, as discussed in detail further below.

Predisposition to cancers, such as breast cancer, and the other cancers identified herein, can be ascertained by testing any tissue of a human for mutations of the A-T gene. For example, a person who has inherited a germline A-T mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the A-T gene. Alteration of a wild-type A-T allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene as large as A-T, manual sequencing is very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

In order to detect the alteration of the wild-type A-T gene in a tissue, it is helpful to isolate the tissue free from surrounding normal tissues. Means for enriching tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

Detection of point mutations may be accomplished by molecular cloning of the A-T allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined.

There are six well known methods for a more complete, yet still indirect, test for confirming the presence of a susceptibility allele: 1) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); and 6) allele-specific PCR (Rano & Kidd, 1989). For allele-specific PCR, primers are used which hybridize at their 3' ends to a particular A-T mutation. If the particular A-T mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the A-T mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type A-T gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the A-T mRNA or gene but can be a segment of either. If the riboprobe comprises only a segment of the A-T mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

DNA sequences of the A-T gene which have been amplified by use of PCR may also be screened using allele-specific probes. These probes are nucleic acid oligomers, each of which contains a region of the A-T gene sequence harboring a known mutation. For example, one oligomer may be about 30 nucleotides in length, corresponding to a portion of the A-T gene sequence. By use of a battery of such allele-specific probes, PCR amplification products can be screened to identify the presence of a previously identified mutation in the A-T gene. Hybridization of allele-specific probes with amplified A-T sequences can be performed, for example, on a nylon filter. Hybridization to a particular probe under stringent hybridization conditions indicates the presence of the same mutation in the tumor tissue as in the allele-specific probe.

Alteration of A-T mRNA expression can be detected by any techniques known in the art. These include Northern blot analysis, PCR amplification and RNase protection. Diminished mRNA expression indicates an alteration of the wild-type A-T gene. Alteration of wild-type A-T genes can also be detected by screening for alteration of wild-type A-T protein. For example, monoclonal antibodies immunoreactive with A-T can be used to screen a tissue. Lack of cognate antigen would indicate an A-T mutation. Antibodies specific for products of mutant alleles could also be used to detect mutant A-T gene product. Such immunological assays can be done in any convenient formats known in the art. These include Western blots, immunohistochemical assays and ELISA assays. Any means for detecting an altered A-T protein can be used to detect alteration of wild-type A-T genes. Functional assays, such as protein binding determinations, can be used. In addition, assays can be used which detect A-T biochemical function. Finding a mutant A-T gene product indicates alteration of a wild-type A-T gene.

Mutant A-T genes or gene products can also be detected in other human body samples, such as serum, stool, urine and sputum. The same techniques discussed above for detection of mutant A-T genes or gene products in tissues can be applied to other body samples. Cancer cells are sloughed off from tumors and appear in such body samples. In addition, the A-T gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant A-T genes or gene products.

The methods of diagnosis of the present invention are applicable to any tumor in which A-T has a role in tumorigenesis. The diagnostic method of the present invention is useful for clinicians, so they can decide upon an appropriate course of treatment.

Primer pairs are useful for determination of the nucleotide sequence of a particular A-T allele using PCR. The pairs of single-stranded DNA primers can be annealed to sequences within or surrounding the A-T gene on chromosome 11q22-23 in order to prime amplifying DNA synthesis of the A-T gene itself. A complete set of these primers allows synthesis of all of the nucleotides of the A-T gene coding sequences, i.e., the exons. The set of primers preferably allows synthesis of both intron and exon sequences. Allele-specific primers can also be used. Such primers anneal only to particular A-T mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from A-T sequences or sequences adjacent to A-T, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the A-T open reading frame as set forth in Genbank accession number U33841 (Savitsky et al. 1995a; Savitsky et al., 1995b; Platzer et al., 1997), design of particular primers is well within the skill of the art.

The nucleic acid probes provided by the present invention are useful for a number of purposes. The probes can be used to detect PCR amplification products. They may also be used to detect mismatches with the A-T gene or mRNA using other techniques.

However, mutations which interfere with the function of the A-T protein are involved in the pathogenesis of cancer. Thus, the presence of an altered (or a mutant) A-T gene which produces a protein having a loss of function, or altered function, directly correlates to an increased risk of cancer. In order to detect a A-T gene mutation, a biological sample is prepared and analyzed for a difference between the sequence of the A-T allele being analyzed and the sequence of the wild-type A-T allele. Mutant A-T alleles can be initially identified by any of the techniques described above. The mutant alleles are then sequenced to identify the specific mutation of the particular mutant allele. Alternatively, mutant A-T alleles can be initially identified by identifying mutant (altered) A-T proteins, using conventional techniques. The mutant alleles are then sequenced to identify the specific mutation for each allele. The mutations, especially those which lead to an altered function of the A-T protein, are then used for the diagnostic and prognostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from the A-T region are preferably complementary to, and hybridize specifically to sequences in the A-T region or in regions that flank a target region therein. A-T sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the A-T polypeptides and fragments thereof or to polynucleotide sequences from the A-T region, particularly from the A-T locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the A-T polypeptide or fragment. Monoclonal antibodies may be made by injecting mice with the protein polypeptides, fusion proteins or fragments thereof. Monoclonal antibodies will be screened by ELISA and tested for specific immunoreactivity with A-T polypeptide or fragments thereof. See, Harlow & Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow & Lane, 1988, or Goding, 1986.

Monoclonal antibodies with affinities of $10^{-8}$ M$^{-1}$ or preferably $10^{-9}$ to $10^{-10}$ M$^{-1}$ or stronger will typically be made by standard procedures as described, e.g., in Harlow & Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"A-T allele" refers to normal alleles of the A-T locus as well as alleles carrying variations that predispose individuals to develop cancer of many sites including, for example, breast, ovarian, cancer. Such predisposing alleles are also called "A-T susceptibility alleles".

"A-T locus," "A-T gene," "A-T Nucleic Acids" or "A-T Polynucleotide" each refer to polynucleotides, all of which are in the A-T region, that are likely to be expressed in normal tissue, certain alleles of which predispose an individual to develop breast, ovarian, cancers. Mutations at the A-T locus may be involved in the initiation and/or progression of other types of tumors. The locus is indicated in part by mutations that predispose individuals to develop cancer. These mutations fall within the A-T region. The A-T locus is intended to include coding sequences, intervening sequences and regulatory elements controlling transcription and/or translation. The A-T locus is intended to include all allelic variations of the DNA sequence.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Probes". Polynucleotide sequence variants associated with A-T alleles which predispose to certain cancers or are associated with most cancers are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/ adventitious bindings, that is, which minimize noise. Since such indications identify neutral DNA polymorphisms as well as mutations, these indications need further analysis to demonstrate detection of an A-T susceptibility allele.

Probes for A-T alleles may be derived from the sequences of the A-T region or its cDNAs. The probes may be of any suitable length, which span all or a portion of the A-T region, and which allow specific hybridization to the A-T region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding A-T are preferred as probes. The probes may also be used to determine whether mRNA encoding A-T is present in a cell or tissue.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie & Fink, 1991.

Methods of Use: Nucleic Acid Diagnosis and Diagnostic Kits

In order to detect the presence of a A-T allele predisposing an individual to cancer, a biological sample such as blood is prepared and analyzed for the presence or absence of susceptibility alleles of A-T. In order to detect the presence of neoplasia, the progression toward malignancy of a precursor lesion, or as a prognostic indicator, a biological sample of the lesion is prepared and analyzed for the presence or absence of mutant alleles of A-T. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant A-T sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 11q. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews & Kricka, 1988; Landegren et al., 1988; Mittlin, 1989; U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding A-T. Allele specific probes are also contemplated within the scope of this invention.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting A-T. Thus, in one example to detect the presence of A-T in a cell sample, more than one probe complementary to A-T is employed and in particular the number of different probes is alternatively 2, 3, or 5 different nucleic acid probe sequences. In another example, to detect the presence of mutations in the A-T gene sequence in a patient, more than one probe complementary to A-T is employed where the cocktail includes probes capable of binding to the allele-specific mutations identified in populations of patients with alterations in A-T. In this embodiment, any number of probes can be used, and will preferably include probes corresponding to the major gene mutations identified as predisposing an individual to breast cancer.

Methods of Use: Peptide Diagnosis and Diagnostic Kits

The neoplastic condition of lesions can also be detected on the basis of the alteration of wild-type A-T polypeptide. Such alterations can be determined by sequence analysis in accordance with conventional techniques. More preferably, antibodies (polyclonal or monoclonal) are used to detect differences in, or the absence of A-T peptides. The antibodies may be prepared as discussed above under the heading "Antibodies". Other techniques for raising and purifying antibodies are well known in the art and any such techniques may be chosen to achieve the preparations claimed in this invention. In a preferred embodiment of the invention, antibodies will immunoprecipitate A-T proteins from solution as well as react with A-T protein on Western or immunoblots of polyacrylamide gels. In another preferred embodiment, antibodies will detect A-T proteins in paraffin or frozen tissue sections, using immunocytochemical techniques.

Preferred embodiments relating to methods for detecting A-T or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference.

The present invention is described by reference to the following Examples, which are offered by way of illustration and are not intended to limit the invention in any manner. Standard techniques well known in the art or the techniques specifically described below were utilized.

EXAMPLE 1

Methods

For genotyping, we obtained DNA samples (from blood or fixed tissue) from A-T homozygotes, who are the index individuals, their nuclear families, and all available blood relatives in their extended families. Informed consent was obtained from each study participant under a protocol approved by the New York Medical College Committee for the Protection of the Rights of Human Subjects. When DNA from a grandmother was not available, but DNA from her husband was, we genotyped the grandmother as a carrier when her husband was not, and vice versa. The requisite DNA samples for determining A-T gene carrier status were available for 99 out of the 261 A-T families participating in our continuing prospective study of mortality and cancer incidence.

Using standard procedures DNA was extracted from the blood lymphocytes of the A-T family members. From paraffin-embedded tissue we directly amplified without a xylene deparaffinization step or DNA extraction (Johnson et al., 1995). Genotyping was done through CA repeat markers D11S1778 and D11S1819 (Gatti et al., 1994) closely flanking the A-T gene locus. In 15 families in which haplotypes based on these two marker loci were not fully informative, D11S1818 (Gatti et al., 1994) and D11S384 (Lench et al., 1994) were also determined. The CA-strand primer was end-labeled with $(\gamma\text{-}^{32}P)ATP$ and PCR was performed using standard conditions. The PCR products were analyzed on a 6% polyacrylamide sequencing gel and autoradiographs were read after 2–4 h exposure.

In two families there was a single recombination between D11S1778 and D11S1819; in both families the haplotype of the A-T chromosome was specified uniquely by D11S384, which shows zero recombination with the A-T locus, (Lench et al., 1994) and D11S1778. Neither of these recombinations affected the genotyping of breast cancer cases. Marker determinations, haplotypes and carrier status were reviewed independently three different times. Of the 775 A-T blood relatives (not obligate heterozygotes or homozygotes) who were genotyped in 99 A-T families, 390 were found to be carriers and 385 non-carriers. The expected numbers were 397.275 and 377.725 respectively.

In the 99 genotyped families, 43 female relatives with breast cancer were identified from our previously published studies, (Swift et al., 1987; Morrell et al., 1990; Swift et al., 1991) from the retrospective data for A-T families incorporated into this study subsequent to those studies, and from our ongoing prospective observation of A-T families. Hospital records from each presumed case were reviewed, prior to knowing the carrier status of the case, to confirm the diagnosis of breast cancer. Ten cases were excluded: two with lobular in situ carcinoma, six for which the marker loci did not amplify cleanly from their tissue sample, and two whose carrier status depended directly on that of another test subject with breast cancer.

Testing the association of A-T heterozygosity with breast cancer through the index-test method requires, in A-T families, determining the A-T gene carrier status of blood relatives with previously identified breast cancers. These test relatives cannot be homozygotes or obligate heterozygotes, whose genotypes are fixed. Both the A-T gene carrier status and relationship of each breast cancer case to the proband in each family were entered into a spreadsheet that calculated the odds ratio, 95% confidence limits, and t-statistic as previously described (Swift et al., 1990a). These calculations were based on comparing the observed number of carriers to the number expected on the basis of Mendelian inheritance and the population frequency of the A-T gene. The prior probability of heterozygosity for the A-T gene is approximately 0.67 for siblings, 0.5 for aunts and grandmothers, and 0.25 for first cousins of the homozygotes.

EXAMPLE 2

Association of A-T with Breast Cancer

In the 99 genotyped families we were able to determine the A-T gene carrier status for 26 women with breast cancer from blood samples, five from fixed tissues, and two others using DNA from the husbands. Thus, 33 breast cancer cases in 28 families were genotyped. Seventeen of these cases had been reported previously (Swift et al., 1987; Morrell et al., 1990; Swift et al., 1991). Only one of the six tissue samples for which PCR was unsuccessful came from an operation in 1980 or later, while four of the five successfully amplified specimens came from operations in 1980 or later (p=0.07).

Of the 33 women with invasive breast cancer, 25 were found to be A-T heterozygotes (Table 1). Ages at the onset of the cancers ranged from 31 to 77. These cancers were diagnosed between 1953 and 1995. Twelve of the breast cancers had occurred in aunts, 13 in grandmothers, five in great-aunts, and one in a sibling, a cousin, and a great-grandmother of an A-T proband. All eight of the non-carrier women, and 17 of the 25 A-T heterozygotes with breast cancer, were living as of Oct. 1, 1995. Five of the carrier women (20%), and two of the non-carriers (25%), had bilateral breast cancer.

TABLE 1

Age at diagnosis for genotyped breast cancers in A–T blood relatives

| Age at diagnosis | A–T heterozygotes | Non-carriers |
|---|---|---|
| 30–34 | 2 | 0 |
| 35–39 | 0 | 0 |
| 40–44 | 1 | 2 |
| 45–49 | 5 | 0 |
| 50–54 | 3 | 3 |
| 55–59 | 4 | 1 |
| 60–64 | 1 | 0 |
| 65–69 | 6 | 1 |
| 70–74 | 2 | 0 |
| 75–79 | 1 | 1 |
| 80+ | 0 | 0 |
| Total | 25 | 8 |

The expected number of A-T heterozygotes in the 33 breast cancer cases was 14.9. If the cancer incidence of carriers and that of non-carriers within the same families were equal, the odds ratio would be approximately one, indicating no association. Instead, for all breast cancers in this sample the odds ratio, which estimates the relative risk of carriers compared to non-carriers, was 3.8 (95% confidence limits 1.7–8.4; one-sided P=0.0001). For the 21 breast cancers with onset before age 60, the odds ratio was 2.9 (1.1–7.6; P=0.009) and for the 12 cases with onset at age 60 or older, the odds ratio was 6.4 (1.4–28.8; P=0.002).

The finding of 25 A-T gene carriers among 33 breast cancer cases in A-T families is compelling evidence that A-T heterozygotes are predisposed to breast cancer. There is no other explanation for this highly significant excess over the 14.9 expected on the basis of Mendelian inheritance and the A-T gene frequency. Since these data come from molecular genotyping, they are fully independent of all previous analyses of breast cancer incidence that compared blood relatives to spouse controls. While the comparison of blood relatives to spouse controls relies on how well these two groups are matched and on the fact that a high proportion of blood relatives are heterozygotes, gene carriers are identified directly with molecular genotyping in the index-test method.

The estimated relative risk, 3.8, of invasive breast cancer for A-T gene carriers compared to non-carriers is close to the most recent previous estimates from the prospective comparison of spouse controls with all blood relatives, 5.1, or with obligate heterozygotes, 3.8 (Swift et al., 1991). The large number of observed breast cancer cases in A-T blood relatives in their 30s, 40s, and 50s suggested previously that the excess breast cancer risk might be especially high for A-T heterozygotes in that age range (Swift et al., 1991). In contrast, molecular genotyping now shows that the relative risk above age 60 may be more than twice that of younger women.

The frequency of A-T heterozygotes in the United States population was estimated by maximum likelihood to be 1.4%, based on the number of families in which A-T homozygotes appeared in more than one sibship in an extended family (Swift et al., 1986). Based on this estimated heterozygote frequency and the estimated relative risks of 2.9 for breast cancers before age 60 and 6.4 for cases with onset after age 60, approximately 6.6% of all breast cancers in the United States occur in A-T heterozygotes [see Table 2]. If the risk of female A-T heterozygotes for breast cancer with onset from age 60 through age 79 is 6.4, then approximately 8.3% of all breast cancers arising in this age group occur in A-T heterozygotes.

TABLE 2

Estimated Frequencies

If the relative risk of breast cancer is 2.9 for cancers with onset before age 60, and the proportion of A–T heterozygotes in the general population is 0.014,
then the ratio of breast cancer cases in A–T heterozygotes
to the total number of
cases with onset before age 60 is given by $\frac{2.9 \times 0.014}{(2.9 \times 0.014) + (1 \times 98.6)}$
or 0.0395.
For breast cancers with onset at age 60 or older, the relative risk is 6.4 and the resulting proportion is 0.0833.
If 40%* of all breast cancers occur before age 60,
then $0.4 \times 0.0395 = 0.01580$ and $0.6 \times 0.0833 = \frac{0.04998}{0.06578}$.

which is the basis for the estimate that 6.6% of
all breast cancer cases occur in
A–T heterozygotes.

*The figure of 40% comes from New York State vital statistics.

Two genes, BRCA1 and BRCA2, that also predispose to breast cancer have been identified through molecular studies of families in which the risk of this cancer is very high (Szabo and King, 1995). The gene frequency of BRCA1 is much greater than that of BRCA2. In contrast to the A-T gene, the risk of breast cancer for BRCA1 gene carriers is highest at young ages; it has been estimated that the proportion of breast cancer cases in the general population due to BRCA1 is 5.3% for onset before age 40 years (Ford et al., 1995). For cases with onset ages 20–69, the estimated proportion is 1.7%. Since about 35% of all breast cancers occur after age 70 (New York State Cancer Registry, 1990), the proportion of BRCA1 carriers in all breast cancer cases is likely to be 1% or less, several fold lower than the estimated proportion of A-T gene carriers among all cases. A direct comparison of the impact of BRCA1, BRCA2, and the A-T gene on breast cancer incidence will be possible when population screening for mutations at these loci becomes practical.

The estimated relative risk of 3.8 is based on breast cancers that occurred in the United States between 1953 and 1995. However, the risk for A-T heterozygotes may vary with different environmental conditions or the genetic composition of a population. Since it will be valuable to attempt to replicate our findings as soon as possible, the risk estimate from our sample of persons of European origin could be compared to an independent estimate readily available through the A-T family registries already established in Europe (Pippard et al., 1988; Borressen et al., 1990; Chessa et al., 1994; Stoppa-Lyonnet et al., 1992). It will also be of great interest to collect family medical data and DNA samples in Africa and Asia to measure this risk in non-European populations.

Previously we found evidence that exposure to certain medical diagnostic X-ray procedures increased the risk of breast cancer for blood relatives in A-T families (Swift et al., 1987; Morrell et al., 1990). If breast cancer with onset above age 60 is more closely associated with A-T heterozygosity than earlier onset breast cancer, as our present data demonstrate, the difference may be explained by increasing exposure to medical diagnostic X-ray procedures with advancing age. Since some of the blood relatives with breast cancer in previous studies may have been non-carriers, we plan to re-examine this issue through a case-control analysis in which the X-ray exposures of identified carriers with breast cancer will be compared to that in matched carrier controls. We plan also to compare the histopathology or survival of A-T gene carriers with breast cancer to that of non-carriers within the same families. There are no data showing that bilateral breast cancer is more frequent among A-T heterozygotes than among non-carriers.

Unlike previous comparisons of blood relatives to spouse controls, these molecular findings cannot be explained by undetected confounders or unintended bias. No confounder can affect the result of the index-test method, since each individual's genotype is fixed at the time of conception. Unintended bias is implausible because the cases were selected, before genotyping, by the single criterion of having hospital record confirmation of breast cancer. The blood relatives did not know their own carrier status at the time they contributed blood samples. If carriers were more likely, because of some behavioral effect of the A-T gene, to contribute blood samples for genotyping than non-carriers, the proportion of carriers and non-carriers among all genotyped blood relatives in these 99 A-T families would have deviated significantly from the expected proportion. Further, it is not possible that more samples were available from breast cancer cases who are carriers because they survive longer, since the proportion of living cases was higher among the non-carriers. If there were an undetected breast cancer risk factor in the genotyped families, it would have affected breast cancer incidence in carriers and non-carriers equally and randomly. It is unlikely that the ability to PCR from stored fixed tissue influenced our result, since this appeared to be a function simply of the length of time specimens were stored.

Carrier determination through highly informative flanking haplotypes was reliable, since we detected no recombination between the closest markers and the A-T locus. Currently available methods for screening for mutations at this locus are tedious and costly, and seem to detect only 50–60% of all such mutations (Savitsky et al., 1995; Byrd et al., 1996; Gilad et al., 1996; Telatar et al., 1996). When population screening for A-T heterozygosity becomes practical, A-T heterozygotes found through such screening could be the index individuals for population based assessments, using the index-test method, of the risk of breast cancer for female A-T heterozygotes.

The A-T alleles segregating in the study families are a random sample of A-T alleles in the general population, since the only distinctive feature of the study families is that two heterozygotes met and had an offspring affected by ataxia-telangiectasia. Families in which this gene is segregating are ideal for testing hypothesized gene-disease associations, since there is natural matching for important risk factors between carriers and non-carriers in these families. It will be of considerable interest to measure the proportion of A-T heterozygotes among breast cancer patients in different populations when population screening is possible. However, comparing these proportions to the general population heterozygote frequency will be less reliable than the index-test method as a test of A-T heterozygote cancer predisposition because of the well-known difficulty in matching populations for confounders, such as ethnicity or social class, that affect both the A-T heterozygote frequency and breast cancer incidence.

Now that the excess risk of breast cancer for A-T heterozygotes has been measured using molecular genotyping and the index-test method, it is imperative to understand the molecular actions of the A-T gene and to identify the environmental and other genetic factors that interact with it to produce cancer.

EXAMPLE 3

Identification of Mutations by Heteroduplex Analysis

Heteroduplex analysis of two of the heterozygous carriers with breast cancer reported above was used to identify two mutations. For heteroduplex analysis each exon of the A-T gene was amplified by the polymerase chain reaction (PCR) using as template genomic DNA from the test subject and primers based on the known A-T gene sequence. The PCR product was then run on an MDE gel which detects heteroduplexes due to differences between the PCR products from the subject's two chromosomes. If there are no differences, then only a single band is seen and there is no sequence variation in that exon in that subject. When an additional band is seen, the PCR products were cloned so that DNA from each chromosome was sequenced. The mutation was verified by comparison of the variant sequence to the known sequence of that exon in the A-T gene (Savitsky et al., 1995a; Savitsky et al., 1995b; Platzer et al., 1997). Further confirmation of the mutation was obtained by sequencing the same exon in close relatives of the subject. With this technique, mutations were identified in the two heterozygotes. The first mutation seen was the nucleotide change ATC→TGAT at base 3245, codon 1082 in exon 24. The second mutation seen was a deletion of 150 basepairs beginning at nucleotide 8269 of codon 2757, leading to the deletion of exon 59. The first mutation predicts a truncation of the protein and the second predicts a deletion of 50 amino acids.

EXAMPLE 4

Identification of Mutations in Families by Sequencing

In this example, each exon of the A-T gene from A-T families with breast cancer was amplified by the polymerase chain reaction (PCR) using as template genomic DNA from the subject and primers based on the known A-T gene sequence. The amplified exons were then sequenced using automated sequencers. In this manner, the exons of the A-T gene from A-T families with breast cancer were sequenced until a mutation was found. The mutation is then confirmed in individual with breast cancer. Using this technique, four mutations in addition to those noted in Example 3 were identified and are set forth in Table 3. The mutations are with respect to the coding sequence of the A-T gene.

TABLE 3

A–T Gene Mutations in Families with Breast Cancer

| Family | Exon | Nucleotide | Mutation |
|--------|------|------------|----------|
| 95     | 20   | 2689       | 5 bp deletion |
| 104    | 12   | 1402       | AA deletion |
| 304    | 10   | 1027       | GAAA deletion |
| 397    | 65   | 9003       | TTT → C |

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Anand, R. (1992). *Techniques for the Analysis of Complex Genomes*, (Academic Press).

Ausubel, F. M., et al. (1992). *Current Protocols in Molecular Biology*, (J. Wiley and Sons, N.Y.)

Boice, J., quoted in Randal, J. (1995). ATM gene discovery may quiet carrier risk debate. *J Natl Cancer Inst* 87:1350–1351.

Borman, S. (1996). *Chemical & Engineering News*, December 9 issue, pp. 42–43.

Borresen, A.-L. et al. (1990). Breast cancer and other cancers in Norwegian families with ataxia-telangiectasia. *Genes Chromosomes Cancer* 2:339–40.

Byrd, P. J. et al. (1996). Mutations revealed by sequencing the 5' half of the gene for ataxia-telangiectasia. *Hum. Mol. Genet.* 5:145–149.

Cariello (1988). *Human Genetics* 42:726.

Chee, M., et al. (1996). *Science* 274:610–614.

Chessa L, et al. (1994). Ataxia-telangiectasia in Italy: genetic analysis (1994). *Int J Radiat Biol* 66 (6 Suppl): S31-3

Collins, F. S. (1996). BRCA1, ATM, and cancer susceptibility. *Proc of the 87th Annual Meeting of the Am Assoc Can Research* 37:670.

Conner, B. J., et al. (1983). *Proc. Natl. Acad. Sci. USA* 80:278–282.

Cotton, et al. (1988). *Proc. Natl. Acad. Sci. USA* 85:4397.

Editorial (1996). *Nature Genetics* 14:367–370.

Elghanian, R., et al. (1997). *Science* 277:1078–1081.

Finkelstein, J., et al. (1990). *Genomics* 7:167–172.

Fodor, S. P. A. (1997). DNA Sequencing. Massively Parallel Genomics. *Science* 277:393–395.

Ford, D. et al. (1995). Estimates of the gene frequency of BRCA1 and its contribution to breast and ovarian cancer incidence. *Am J Hum Genet* 57:1457–1462.

Gatti, R. A. et al. (1994). Genetic haplotyping of ataxia-telangiectasia families localizes the major gene to an ≈850 kb region on chromosome 11q23.1. *Int J Radiat Biol* 66:S57–62.

Gilad, S. et al. (1996). Predominance of null mutations in ataxia-telangiectasia. *Hum Molec Genet* 5:433–439.

Glover, D. (1985). *DNA Cloning*, I and II (Oxford Press).

Goding (1986). *Monoclonal Antibodies: Principles and Practice*, 2d ed. (Academic Press, N.Y.).

Grompe, M., (1993). *Nature Genetics* 5:111–117.
Grompe, M., et al., (1989). *Proc. Natl. Acad. Sci. USA* 86:5855–5892.
Guthrie, G. & Fink, G. R. (1991). *Guide to Yeast Genetics and Molecular Biology* (Academic Press).
Hacia, J. G., et al. (1996). *Nature Genetics* 14:441–447.
Harlow & Lane (1988). *Antibodies: A Laboratory Manual* (Cold Spring Harbor Laboratory, Cold Spring Harbor, N.Y.
Huse, et al. (1989). *Science* 246:1275–1281.
2Innis et al. (1990). *PCR Protocols: A Guide to Methods and Applications* (Academic Press, San Diego, Calif.).
Jablonski, E., et al. (1986). *Nuc. Acids Res.* 14:6115–6128.
Johnson, D. R. et al. (1995). Direct molecular analysis of archival tumor tissue for loss of heterozygosity. *Biotech* 19:190–191.
Kasten, M. (1995) Ataxia-telangiectasia—broad implications for a rare disorder. *New Eng J Med* 333:662–663.
Kinszler, K. W., et al. (1991). *Science* 251:1366–1370.
Landegren, et al (1988). *Science* 242:229.
Lench, N. J. et al. (1994). The DNA marker D11S384 shows zero recombination with the ataxia-telangiectasia locus in North American families. *Int J Rad Biol* 66:S67-S69.
Lipshutz, R. J., et al. (1995). *Biotechniques* 19:442–447.
Lockhart, D. J., et al. (1996). *Nature Biotechnology* 14:1675–1680.
Maniatis. T., et al. (1982). *Molecular Cloning: A Laboratory Manual* (Cold Spring Harbor Laboratory, Cold Spring Harbor, N.Y.).
Martin, R., et al. (1990). *BioTechniques* 9:762–768.
Matthews & Kricka (1988). *Anal. Biochem.* 169:1.
Mittlin (1989). *Clinical Chem.* 35:1819.
Modrich, P. (1991). *Ann. Rev. Genet.* 25:229–253.
Morrell, D. et al. (1986). Mortality and cancer incidence in 263 patients with ataxia-telangiectasia (1986). *J Nat Cancer Inst* 77:89–92.
Morrell, D. et al. (1990). Cancers in 44 families with ataxia-telangiectasia. *Cancer Genet Cytogenet* 50: 119123.
Newton, C. R. et al. (1989). *Nuc. Acids Res.* 17:2503–2516.
New York State Cancer Registry, Time Trends in Cancer Incidence, 1977–1986 (1990). State of New York, Department of health.
Nguyen, Q., et al. (1992). *BioTechniques* 13:116–123.
Novack, et al. (1986). *Proc. Natl. Acad. Sci. USA* 83:586.
Orita, et al. (1989). *Proc. Natl. Acad. Sci. USA* 86:2776-2770.
Pippard, E. C. et al. (1988). Cancer in homozygotes and heterozygotes of ataxia-telangiectasia and xeroderma pigmentosum in Britain. *Cancer Res* 48:2929–32.
Platzer, M. et al. (1997). *Genome Res.* 7:592–605.
Rano & Kidd (1989). *Nucl. Acids Res.* 17:8392.
Rigby, P. W. J., et al. (1977). *J. Mol. Biol.* 113:237–251.
Sambrook, J., et al. (1989). *Molecular Cloning: A Laboratory Manual,* 2nd Ed. (Cold Spring Harbor Laboratory, Cold Spring Harbor, N.Y.).
Savitsky, K. et al. (1995a). A Single Ataxia Telangiectasia Gene with a Product Similar to PI-3 Kinase. *Science* 268:1749–1753.
Savitsky, K. et al. (1995b). The complete sequence of the coding region of the ATM gene reveals similarity to cell cycle regulators in different species. *Hum Gen Genetics* 4:2025–2032.
Scharf (1986). *Science* 233:1076.
Sheffield, V. C., et al. (1989). *Proc. Natl. Acad. Sci. USA* 86:232–236.
Sheffield, V. C., et al. (1991). *Am. J. Hum. Genet.* 49:699–706.
Shenk, et al. (1975). *Proc. Natl. Acad. Sci USA* 72:989.
Stoppa-Lyonnet, D. and Aurias, A. (1992). Ataxia-telangiectasia: what impact in clinical oncology. *Bull Cancer Paris* 79:645–50
Swift, M. (1993). Genetic aspects of ataxia-telangiectasia. *Adv Neurol* 61:115–235.
Swift, M. et al. (1976). Malignant neoplasms in the families of patients with ataxia-telangiectasia. *Cancer Res* 36:209–215.
Swift, M. et al. (1986). The incidence and gene frequency of ataxia-telangiectasia in the United States. *Am J Hum Genet* 39:573–583.
Swift, M. et al. (1987). Breast and other cancers in families with ataxia-telangiectasia. *N Engl J Med* 316:1289–1294.
Swift, M. et al. (1990a). Effective testing of gene-disease associations. *Am J Hum Genet* 47:266–274.
Swift, M. et al. (1990b). Cancer predisposition of ataxia-telangiectasia heterozygotes. *Cancer Genet Cytogenet* 46:21–27.
Swift, M. et al. (1991). Incidence of cancer in 161 families affected by ataxia-telangiectasia. *N Engl J Med* 325:1831–1836.
Szabo, C. I. and King, M. C. (1995). Inherited breast and ovarian cancer. *Hum Molec Genet* 4:1811–7.
Telatar, M. et al. (1996). Ataxia-telangiectasia: Mutations in ATM cDNA detected by protein-truncation screening. *Am J Hum Genet* 59:40–44.
Wartell, R. M., et al. (1990). *Nucl. Acids Res.* 18:2699–2705.
White, M. B., et al., (1992). *Genomics* 12:301–306.
Wu, et al. (1989a). *Genomics* 4:560–569.

What is claimed is:

1. A method for predicting a predisposition to breast cancer in an individual comprising:

determining the presence of an alteration in the germline A-T nucleic acid sequence from said individual as compared to the wildtype germline A-T nucleic acid sequence, wherein the germline alteration is an A-T susceptibility allele statistically associated with a predisposition to breast cancer.

2. The method of claim 1, wherein determining the presence of an alteration in the germline A-T nucleic acid sequence further comprises the steps of:

obtaining a sample which contains nucleic acid from said individual;

screening for the presence of said germline A-T nucleic acid sequence in said sample;

sequencing said germline A-T nucleic acid sequence in said sample; and determining the presence of an alteration in said germline A-T nucleic acid sequence.

3. The method of claim 2, wherein said nucleic acid is DNA selected from the group consisting of cDNA, ssDNA, dsDNA, and genomic DNA.

4. The method of claim 2, wherein said nucleic acid is RNA selected from the group consisting of mRNA, dsRNA, and ssRNA.

5. The method of claim 2, wherein said determining the presence of an alteration is performed by one or more methods selected from the group consisting of direct DNA sequencing, SSCA, CDGE, HA, CMC, DGGE, RNase protection assays, ASOs, and allele-specific PCR.

6. The method of claim 2, wherein said sample comprises a human tissue.

7. The method of claim 2, wherein said sample comprises a human cell type.

8. The method of claim 2, wherein said sample is a biological sample.

9. The method of claim 1, wherein said alteration comprises a mutation in said germline A-T nucleic acid sequence.

10. The method of claim 9, wherein said mutation occurs in the coding region of said germline A-T nucleic acid sequence.

11. The method of claim 9, wherein said mutation is one or more selected from the group consisting of point mutations, insertions, and deletions.

12. The method of claim 9, wherein said mutation in said germline A-T nucleic acid sequence is selected from the group the group consisting of 3245 ATC→TGAT, 8269 del 150, 2689 del 5, 1402 del AA, 1027 del GAAA, and 9003 TTT-C.

* * * * *